US006696410B1

(12) United States Patent
Lee et al.

(10) Patent No.: US 6,696,410 B1
(45) Date of Patent: Feb. 24, 2004

(54) COMPOSITIONS AND THERAPEUTIC METHODS USING MORPHOGENIC PROTEINS, HORMONES AND HORMONE RECEPTORS

(75) Inventors: John C. Lee, San Antonio, TX (US); Lee-Chuan C. Yeh, San Antonio, TX (US)

(73) Assignee: Stryker Corporation, Kalamazoo, MI (US)

( * ) Notice: Subject to any disclaimer, the term of this patent is extended or adjusted under 35 U.S.C. 154(b) by 29 days.

(21) Appl. No.: 09/672,224

(22) Filed: Sep. 27, 2000

Related U.S. Application Data

(60) Provisional application No. 60/156,261, filed on Sep. 27, 1999.

(51) Int. Cl.[7] ........................ A61K 38/00; A61K 39/00; C07K 14/00

(52) U.S. Cl. ........................... 514/2; 530/350; 530/399; 424/198.1

(58) Field of Search .............................. 514/2; 530/350, 530/399; 424/198.1

(56) References Cited

U.S. PATENT DOCUMENTS 5,141,905 A * 8/1992 Rosen et al. ............. 435/235.1

FOREIGN PATENT DOCUMENTS

| | | |
|---|---|---|
| WO | WO 97/21447 | 6/1997 |
| WO | WO 99/21574 | 5/1999 |

OTHER PUBLICATIONS

Mundy et al. , Bone, 1195, vol. 17 (2 suppl.), pp. 71S–75S.*

T. Bellido et al., "Transcriptional Activation of the $p21^{WAF1, CIP1, SDI1}$ Gene Interleukin–6 Type Cytokines, A Prerequisite for Their Pro–Differentiating and Anti–apoptotic Effects on Human Osteoblastic Cells," *J. Biol. Chem.* 273:21137–44 (1998).

N. Franchimont et al., "Interleukin–6 with Its Soluble Receptor Enhances the Expression of Insulin–Like Growth Factor–I in Osteoblasts," *Endocrinology* 138:5248–55 (1997).

S. Manolagas, "The Role of IL–6 Type Cytokines and Their Receptors in Bone," *Ann. N.Y. Acad. Sci.* 840:194–204 (1998).

M. Peters et al., "The Function of the Soluble Interleukin 6 (IL–6) Receptor In Vivo: Sensitization of Human Soluble IL–6 Receptor Transgenic Mice Towards IL–6 and Prolongation of the Plasma Half–life of IL–6", *J. Exp. Med.* 183:1399–406 (1996).

S. Rose–John et al., "The Soluble Interleukin–6 Receptor," *Ann. N.Y. Acad. Sci.* 762:207–21 (1995) (see especially discussion at pp. 220–221).

Taguchi et al., "Interleukin–6 –type Cytokines Stimulate Mesenchymal Progenitor Differentiation Toward the Osteoblastic Lineage", *Proc. Assoc. Am. Physicians* 110:559–74 (1998).

Ebendal et al., "Bone Morphogenetic Proteins and Their Receptors: Potential Functions in the Brain," *J. of Neuroscience Research* 51:139–146 (1998).

Guo et al., "Leukemia Inhibitory Factor and Ciliary Neurotrophic Factor Cause Dendtritic Retraction in Cultured Rat Sympathetic Neurons," *J. of Neuroscience*, 19(6):2113–2121 (1999).

Reddi et al., "Initiation and Promotion of Bone Differentiation by Bone Morphogenetic Proteins," *J. of Bone and Mineral Research*, vol. 8, Suppl. 2:S499–S502 (1993).

Rose–John et al., "Soluble receptors for cytokines and growth factors: generation and biological function," *Biochem. J.,* 308:281–290 (1994).

* cited by examiner

*Primary Examiner*—Yvonne Eyler
*Assistant Examiner*—Janet L. Andres
(74) *Attorney, Agent, or Firm*—Fish & Neave; James F. Haley, Jr.; Haitao Sun

(57) ABSTRACT

This invention features devices and methods for inducing tissue formation in a mammal, involving the use of a morphogenic protein, a hormone and a soluble receptor of the hormone. The hormone and receptor thereof are used to enhance the tissue inductive activity of the morphogenic protein.

27 Claims, 5 Drawing Sheets

SEQUENCE LISTING

```
<160> NUMBER OF SEQ ID NOS: 14

<210> SEQ ID NO 1
<211> LENGTH: 1822
<212> TYPE: DNA
<213> ORGANISM: Homo sapiens
<220> FEATURE:
<221> NAME/KEY: CDS
<222> LOCATION: (49)..(1341)

<400> SEQUENCE: 1

ggtgcgggcc cggagcccgg agcccgggta gcgcgtagag ccggcgcg atg cac gtg      57
                                                     Met His Val
                                                       1

cgc tca ctg cga gct gcg gcg ccg cac agc ttc gtg gcg ctc tgg gca      105
Arg Ser Leu Arg Ala Ala Ala Pro His Ser Phe Val Ala Leu Trp Ala
      5                  10                  15

ccc ctg ttc ctg ctg cgc tcc gcc ctg gcc gac ttc agc ctg gac aac      153
Pro Leu Phe Leu Leu Arg Ser Ala Leu Ala Asp Phe Ser Leu Asp Asn
 20                  25                  30                  35

gag gtg cac tcg agc ttc atc cac cgg cgc ctc cgc agc cag gag cgg      201
Glu Val His Ser Ser Phe Ile His Arg Arg Leu Arg Ser Gln Glu Arg
                 40                  45                  50

cgg gag atg cag cgc gag atc ctc tcc att ttg ggc ttg ccc cac cgc      249
Arg Glu Met Gln Arg Glu Ile Leu Ser Ile Leu Gly Leu Pro His Arg
             55                  60                  65

ccg cgc ccg cac ctc cag ggc aag cac aac tcg gca ccc atg ttc atg      297
Pro Arg Pro His Leu Gln Gly Lys His Asn Ser Ala Pro Met Phe Met
         70                  75                  80

ctg gac ctg tac aac gcc atg gcg gtg gag gag ggc ggc ggg ccc ggc      345
Leu Asp Leu Tyr Asn Ala Met Ala Val Glu Glu Gly Gly Gly Pro Gly
     85                  90                  95

ggc cag ggc ttc tcc tac ccc tac aag gcc gtc ttc agt acc cag ggc      393
Gly Gln Gly Phe Ser Tyr Pro Tyr Lys Ala Val Phe Ser Thr Gln Gly
100                 105                 110                 115

ccc cct ctg gcc agc ctg caa gat agc cat ttc ctc acc gac gcc gac      441
Pro Pro Leu Ala Ser Leu Gln Asp Ser His Phe Leu Thr Asp Ala Asp
                120                 125                 130

atg gtc atg agc ttc gtc aac ctc gtg gaa cat gac aag gaa ttc ttc      489
Met Val Met Ser Phe Val Asn Leu Val Glu His Asp Lys Glu Phe Phe
            135                 140                 145

cac cca cgc tac cac cat cga gag ttc cgg ttt gat ctt tcc aag atc      537
His Pro Arg Tyr His His Arg Glu Phe Arg Phe Asp Leu Ser Lys Ile
        150                 155                 160

cca gaa ggg gaa gct gtc acg gca gcc gaa ttc cgg atc tac aag gac      585
Pro Glu Gly Glu Ala Val Thr Ala Ala Glu Phe Arg Ile Tyr Lys Asp
    165                 170                 175

tac atc cgg gaa cgc ttc gac aat gag acg ttc cgg atc agc gtt tat      633
Tyr Ile Arg Glu Arg Phe Asp Asn Glu Thr Phe Arg Ile Ser Val Tyr
180                 185                 190                 195

cag gtg ctc cag gag cac ttg ggc agg gaa tcg gat ctc ttc ctg ctc      681
Gln Val Leu Gln Glu His Leu Gly Arg Glu Ser Asp Leu Phe Leu Leu
                200                 205                 210

gac agc cgt acc ctc tgg gcc tcg gag gag ggc tgg ctg gtg ttt gac      729
Asp Ser Arg Thr Leu Trp Ala Ser Glu Glu Gly Trp Leu Val Phe Asp
            215                 220                 225

atc aca gcc acc agc aac cac tgg gtg gtc aat ccg cgg cac aac ctg      777
Ile Thr Ala Thr Ser Asn His Trp Val Val Asn Pro Arg His Asn Leu
        230                 235                 240
```

-continued

```
ggc ctg cag ctc tcg gtg gag acg ctg gat ggg cag agc atc aac ccc      825
Gly Leu Gln Leu Ser Val Glu Thr Leu Asp Gly Gln Ser Ile Asn Pro
    245                 250                 255

aag ttg gcg ggc ctg att ggg cgg cac ggg ccc cag aac aag cag ccc      873
Lys Leu Ala Gly Leu Ile Gly Arg His Gly Pro Gln Asn Lys Gln Pro
260                 265                 270                 275

ttc atg gtg gct ttc ttc aag gcc acg gag gtc cac ttc cgc agc atc      921
Phe Met Val Ala Phe Phe Lys Ala Thr Glu Val His Phe Arg Ser Ile
                280                 285                 290

cgg tcc acg ggg agc aaa cag cgc agc cag aac cgc tcc aag acg ccc      969
Arg Ser Thr Gly Ser Lys Gln Arg Ser Gln Asn Arg Ser Lys Thr Pro
            295                 300                 305

aag aac cag gaa gcc ctg cgg atg gcc aac gtg gca gag aac agc agc     1017
Lys Asn Gln Glu Ala Leu Arg Met Ala Asn Val Ala Glu Asn Ser Ser
        310                 315                 320

agc gac cag agg cag gcc tgt aag aag cac gag ctg tat gtc agc ttc     1065
Ser Asp Gln Arg Gln Ala Cys Lys Lys His Glu Leu Tyr Val Ser Phe
    325                 330                 335

cga gac ctg ggc tgg cag gac tgg atc atc gcg cct gaa ggc tac gcc     1113
Arg Asp Leu Gly Trp Gln Asp Trp Ile Ile Ala Pro Glu Gly Tyr Ala
340                 345                 350                 355

gcc tac tac tgt gag ggg gag tgt gcc ttc cct ctg aac tcc tac atg     1161
Ala Tyr Tyr Cys Glu Gly Glu Cys Ala Phe Pro Leu Asn Ser Tyr Met
                360                 365                 370

aac gcc acc aac cac gcc atc gtg cag acg ctg gtc cac ttc atc aac     1209
Asn Ala Thr Asn His Ala Ile Val Gln Thr Leu Val His Phe Ile Asn
            375                 380                 385

ccg gaa acg gtg ccc aag ccc tgc tgt gcg ccc acg cag ctc aat gcc     1257
Pro Glu Thr Val Pro Lys Pro Cys Cys Ala Pro Thr Gln Leu Asn Ala
        390                 395                 400

atc tcc gtc ctc tac ttc gat gac agc tcc aac gtc atc ctg aag aaa     1305
Ile Ser Val Leu Tyr Phe Asp Asp Ser Ser Asn Val Ile Leu Lys Lys
    405                 410                 415

tac aga aac atg gtg gtc cgg gcc tgt ggc tgc cac tagctcctcc          1351
Tyr Arg Asn Met Val Val Arg Ala Cys Gly Cys His
420                 425                 430

gagaattcag accctttggg gccaagtttt tctggatcct ccattgctcg ccttggccag   1411

gaaccagcag accaactgcc ttttgtgaga ccttcccctc cctatcccca actttaaagg   1471

tgtgagagta ttaggaaaca tgagcagcat atggcttttg atcagttttt cagtggcagc   1531

atccaatgaa caagatccta caagctgtgc aggcaaaacc tagcaggaaa aaaaaacaac   1591

gcataaagaa aaatggccgg gccaggtcat tggctgggaa gtctcagcca tgcacggact   1651

cgtttccaga ggtaattatg agcgcctacc agccaggcca cccagccgtg ggaggaaggg   1711

ggcgtggcaa ggggtgggca cattggtgtc tgtgcgaaag gaaaattgac ccggaagttc   1771

ctgtaataaa tgtcacaata aaacgaatga atgaaaaaaa aaaaaaaaaa a            1822


<210> SEQ ID NO 2
<211> LENGTH: 431
<212> TYPE: PRT
<213> ORGANISM: Homo sapiens

<400> SEQUENCE: 2

Met His Val Arg Ser Leu Arg Ala Ala Ala Pro His Ser Phe Val Ala
  1               5                  10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
```

-continued

```
        35                  40                  45

Gln Glu Arg Arg Glu Met Gln Arg Glu Ile Leu Ser Ile Leu Gly Leu
     50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 3
<211> LENGTH: 102
<212> TYPE: PRT
<213> ORGANISM: Artificial Sequence
```

-continued

<220> FEATURE:
<223> OTHER INFORMATION: Description of Artificial Sequence: OPX
<220> FEATURE:
<223> OTHER INFORMATION: Each Xaa is independently selected from a group of one or more specified amino acids as defined in the specification.

<400> SEQUENCE: 3

Cys Xaa Xaa His Glu Leu Tyr Val Ser Phe Xaa Asp Leu Gly Trp Xaa
1 5 10 15

Asp Trp Xaa Ile Ala Pro Xaa Gly Tyr Xaa Ala Tyr Tyr Cys Glu Gly
20 25 30

Glu Cys Xaa Phe Pro Leu Xaa Ser Xaa Met Asn Ala Thr Asn His Ala
35 40 45

Ile Xaa Gln Xaa Leu Val His Xaa Xaa Xaa Pro Xaa Xaa Val Pro Lys
50 55 60

Xaa Cys Cys Ala Pro Thr Xaa Leu Xaa Ala Xaa Ser Val Leu Tyr Xaa
65 70 75 80

Asp Xaa Ser Xaa Asn Val Ile Leu Xaa Lys Xaa Arg Asn Met Val Val
85 90 95

Xaa Ala Cys Gly Cys His
100

<210> SEQ ID NO 4
<211> LENGTH: 97
<212> TYPE: PRT
<213> ORGANISM: Artificial Sequence
<220> FEATURE:
<223> OTHER INFORMATION: Description of Artificial Sequence: Generic-Seq-7
<220> FEATURE:
<223> OTHER INFORMATION: Each Xaa is independently selected from a group of one or more specified amino acids as defined in the specification.

<400> SEQUENCE: 4

Leu Xaa Xaa Xaa Phe Xaa Xaa Xaa Gly Trp Xaa Xaa Xaa Xaa Xaa Xaa
1 5 10 15

Pro Xaa Xaa Xaa Xaa Ala Xaa Tyr Cys Xaa Gly Xaa Cys Xaa Xaa Pro
20 25 30

Xaa Xaa Xaa Xaa Xaa Xaa Xaa Xaa Asn His Ala Xaa Xaa Xaa Xaa Xaa
35 40 45

Xaa Xaa Xaa Xaa Xaa Xaa Xaa Xaa Xaa Xaa Xaa Xaa Cys Cys Xaa Pro
50 55 60

Xaa Xaa Xaa Xaa Xaa Xaa Xaa Xaa Leu Xaa Xaa Xaa Xaa Xaa Xaa Xaa
65 70 75 80

Val Xaa Leu Xaa Xaa Xaa Xaa Xaa Met Xaa Val Xaa Xaa Cys Xaa Cys
85 90 95

Xaa

<210> SEQ ID NO 5
<211> LENGTH: 102
<212> TYPE: PRT
<213> ORGANISM: Artificial Sequence
<220> FEATURE:
<223> OTHER INFORMATION: Description of Artificial Sequence: Generic-Seq-8
<220> FEATURE:
<223> OTHER INFORMATION: Each Xaa is independently selected from a group of one or more specified amino acids as defined in the specification.

<400> SEQUENCE: 5

-continued

```
Cys Xaa Xaa Xaa Xaa Leu Xaa Xaa Xaa Phe Xaa Xaa Xaa Gly Trp Xaa
  1               5                  10                  15

Xaa Xaa Xaa Xaa Xaa Pro Xaa Xaa Xaa Xaa Ala Xaa Tyr Cys Xaa Gly
             20                  25                  30

Xaa Cys Xaa Xaa Pro Xaa Xaa Xaa Xaa Xaa Xaa Xaa Xaa Asn His Ala
         35                  40                  45

Xaa Xaa Xaa Xaa Xaa Xaa Xaa Xaa Xaa Xaa Xaa Xaa Xaa Xaa Xaa Xaa
     50                  55                  60

Xaa Cys Cys Xaa Pro Xaa Xaa Xaa Xaa Xaa Xaa Xaa Xaa Leu Xaa Xaa
 65                  70                  75                  80

Xaa Xaa Xaa Xaa Xaa Val Xaa Leu Xaa Xaa Xaa Xaa Xaa Met Xaa Val
                 85                  90                  95

Xaa Xaa Cys Xaa Cys Xaa
             100
```

<210> SEQ ID NO 6
<211> LENGTH: 97
<212> TYPE: PRT
<213> ORGANISM: Artificial Sequence
<220> FEATURE:
<223> OTHER INFORMATION: Description of Artificial Sequence: Generic-Seq-9
<220> FEATURE:
<223> OTHER INFORMATION: Each Xaa is independently selected from a group of one or more specified amino acids as defined in the specification.

<400> SEQUENCE: 6

```
Xaa Xaa Xaa Xaa Xaa Xaa Xaa Xaa Xaa Xaa Xaa Xaa Xaa Xaa Xaa Xaa
  1               5                  10                  15

Pro Xaa Xaa Xaa Xaa Xaa Xaa Xaa Cys Xaa Gly Xaa Cys Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Cys Xaa Pro
     50                  55                  60

Xaa Xaa Xaa Xaa Xaa Xaa Xaa Xaa Leu Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Cys Xaa Cys
                 85                  90                  95

Xaa
```

<210> SEQ ID NO 7
<211> LENGTH: 102
<212> TYPE: PRT
<213> ORGANISM: Artificial Sequence
<220> FEATURE:
<223> OTHER INFORMATION: Description of Artificial Sequence: Generic-Seq-10
<220> FEATURE:
<223> OTHER INFORMATION: Each Xaa is independently selected from a group of one or more specified amino acids as defined in the specification.

<400> SEQUENCE: 7

```
Cys Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Pro Xaa Xaa Xaa Xaa Xaa Xaa Xaa Cys Xaa Gly
             20                  25                  30

Xaa Cys Xaa Xaa Xaa Xaa Xaa Xaa Xaa Xaa Xaa Xaa Xaa Xaa Xaa Xaa
```

-continued

```
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Cys Xaa Pro Xaa Xaa Xaa Xaa Xaa Xaa Xaa Xaa Leu Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Cys Xaa Cys Xaa
            100


<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<223> OTHER INFORMATION: Each Xaa is independently selected from a
      group of one or more specified amino acids as
      defined in the specification.

<400> SEQUENCE: 8

Cys Xaa Xaa Xaa Xaa
  1               5


<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<223> OTHER INFORMATION: Each Xaa is independently selected from a
      group of one or more specified amino acids as
      defined in the specification.

<400> SEQUENCE: 9

Cys Xaa Xaa Xaa Xaa
  1               5


<210> SEQ ID NO 10
<211> LENGTH: 102
<212> TYPE: PRT
<213> ORGANISM: Artificial Sequence
<220> FEATURE:
<223> OTHER INFORMATION: Description of Artificial Sequence: Generic
      amino acid sequence
<220> FEATURE:
<223> OTHER INFORMATION: Each Xaa may be any amino acid residue

<400> SEQUENCE: 10

Cys Xaa Xaa Xaa Xaa Leu Xaa Val Xaa Phe Xaa Asp Xaa Gly Trp Xaa
  1               5                  10                  15

Xaa Trp Xaa Xaa Xaa Pro Xaa Gly Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

Xaa Xaa Gln Xaa Xaa Val Xaa Xaa Xaa Asn Xaa Xaa Xaa Xaa Pro Xaa
    50                  55                  60

Xaa Cys Cys Xaa Pro Xaa Xaa Xaa Xaa Xaa Xaa Xaa Xaa Leu Xaa Xaa
 65                  70                  75                  80

Xaa Xaa Xaa Xaa Xaa Val Xaa Leu Xaa Xaa Tyr Xaa Xaa Met Xaa Val
```

-continued

```
                 85                  90                  95

Xaa Xaa Cys Xaa Cys Xaa
            100


<210> SEQ ID NO 11
<211> LENGTH: 96
<212> TYPE: PRT
<213> ORGANISM: Artificial Sequence
<220> FEATURE:
<223> OTHER INFORMATION: Description of Artificial Sequence: Synthetic
      amino acid (COP5)

<400> SEQUENCE: 11

Leu Tyr Val Asp Phe Ser Asp Val Gly Trp Asp Asp Trp Ile Val Ala
  1               5                  10                  15

Pro Pro Gly Tyr Gln Ala Phe Tyr Cys His Gly Glu Cys Pro Phe Pro
             20                  25                  30

Leu Ala Asp His Phe Asn Ser Thr Asn His Ala Val Val Gln Thr Leu
         35                  40                  45

Val Asn Ser Val Asn Ser Lys Ile Pro Lys Ala Cys Cys Val Pro Thr
     50                  55                  60

Glu Leu Ser Ala Ile Ser Met Leu Tyr Leu Asp Glu Asn Glu Lys Val
 65                  70                  75                  80

Val Leu Lys Tyr Asn Gln Glu Met Val Val Glu Gly Cys Gly Cys Arg
                 85                  90                  95


<210> SEQ ID NO 12
<211> LENGTH: 96
<212> TYPE: PRT
<213> ORGANISM: Artificial Sequence
<220> FEATURE:
<223> OTHER INFORMATION: Description of Artificial Sequence: Synthetic
      amino acid (COP7)

<400> SEQUENCE: 12

Leu Tyr Val Asp Phe Ser Asp Val Gly Trp Asn Asp Trp Ile Val Ala
  1               5                  10                  15

Pro Pro Gly Tyr His Ala Phe Tyr Cys His Gly Glu Cys Pro Phe Pro
             20                  25                  30

Leu Ala Asp His Leu Asn Ser Thr Asn His Ala Val Val Gln Thr Leu
         35                  40                  45

Val Asn Ser Val Asn Ser Lys Ile Pro Lys Ala Cys Cys Val Pro Thr
     50                  55                  60

Glu Leu Ser Ala Ile Ser Met Leu Tyr Leu Asp Glu Asn Glu Lys Val
 65                  70                  75                  80

Val Leu Lys Tyr Asn Gln Glu Met Val Val Glu Gly Cys Gly Cys Arg
                 85                  90                  95


<210> SEQ ID NO 13
<211> LENGTH: 97
<212> TYPE: PRT
<213> ORGANISM: Artificial Sequence
<220> FEATURE:
<223> OTHER INFORMATION: Description of Artificial Sequence: Generic
      amino acid sequence
<220> FEATURE:
<221> NAME/KEY: MISC_FEATURE
<222> LOCATION: (2)..(2)
<223> OTHER INFORMATION: Xaa2 = (Tyr, Lys or Phe)
<220> FEATURE:
<221> NAME/KEY: MISC_FEATURE
<222> LOCATION: (4)..(4)
<223> OTHER INFORMATION: Xaa4 = (Asp, Ser or Glu)
```

-continued

```
<220> FEATURE:
<221> NAME/KEY: MISC_FEATURE
<222> LOCATION: (6)..(6)
<223> OTHER INFORMATION: Xaa6 = (Arg, Ser, Lys or Ala)
<220> FEATURE:
<221> NAME/KEY: MISC_FEATURE
<222> LOCATION: (8)..(8)
<223> OTHER INFORMATION: Xaa8 = (Val, Leu or Ile)
<220> FEATURE:
<221> NAME/KEY: MISC_FEATURE
<222> LOCATION: (11)..(12)
<223> OTHER INFORMATION: Xaa11 = (Asn, Gln, Asp or Ser); Xaa12 = (Asp,
      Glu or Asn)
<220> FEATURE:
<221> NAME/KEY: MISC_FEATURE
<222> LOCATION: (14)..(16)
<223> OTHER INFORMATION: Xaa14 = (Ile or Val); Xaa15 = (Val or Ile);
      Xaa16 = (Ala or Ser)
<220> FEATURE:
<221> NAME/KEY: MISC_FEATURE
<222> LOCATION: (18)..(18)
<223> OTHER INFORMATION: Xaa18 = (Pro, Glu, Leu or Lys)
<220> FEATURE:
<221> NAME/KEY: MISC_FEATURE
<222> LOCATION: (20)..(21)
<223> OTHER INFORMATION: Xaa20 = (Tyr or Phe); Xaa21 = (His or Asp)
<220> FEATURE:
<221> NAME/KEY: MISC_FEATURE
<222> LOCATION: (23)..(23)
<223> OTHER INFORMATION: Xaa23 = (Phe, Tyr or Asn)
<220> FEATURE:
<221> NAME/KEY: MISC_FEATURE
<222> LOCATION: (26)..(26)
<223> OTHER INFORMATION: Xaa26 = (His, Glu or Ser)
<220> FEATURE:
<221> NAME/KEY: MISC_FEATURE
<222> LOCATION: (28)..(28)
<223> OTHER INFORMATION: Xaa28 = (Glu or Ala)
<220> FEATURE:
<221> NAME/KEY: MISC_FEATURE
<222> LOCATION: (30)..(31)
<223> OTHER INFORMATION: Xaa30 = (Pro, Ala or Gln); Xaa31 = (Phe or Tyr)
<220> FEATURE:
<221> NAME/KEY: MISC_FEATURE
<222> LOCATION: (33)..(40)
<223> OTHER INFORMATION: Xaa33 = (Leu, Met or Ile); Xaa34 = (Ala, Pro or
      Thr); Xaa35 = (Asp, Glu or Lys); Xaa36 = (His or Ser); Xaa37 =
      (Leu, Met or Phe); Xaa38 = (Asn or Lys); Xaa39 = (Ser, Ala or
      Pro); Xaa40 = (Thr or Ser)
<220> FEATURE:
<221> NAME/KEY: MISC_FEATURE
<222> LOCATION: (44)..(45)
<223> OTHER INFORMATION: Xaa44 = (Ile, Val or Thr); Xaa45 = (Val, Ile
      or Leu)
<220> FEATURE:
<221> NAME/KEY: MISC_FEATURE
<222> LOCATION: (47)..(48)
<223> OTHER INFORMATION: Xaa47 = (Thr or Ser); Xaa48 = (Leu or Ile)
<220> FEATURE:
<221> NAME/KEY: MISC_FEATURE
<222> LOCATION: (50)..(52)
<223> OTHER INFORMATION: Xaa50 = (Asn, His or Arg); Xaa51 = (Ser, Ala,
      Phe or Asn); Xaa52 = (Val or Ile)
<220> FEATURE:
<221> NAME/KEY: MISC_FEATURE
<222> LOCATION: (54)..(57)
<223> OTHER INFORMATION: Xaa54 = (Pro or Ser); Xaa55 =
      (Gly or Glu); Xaa56 = (Lys, Gln, Thr or Ser); Xaa57 = (Ile or Val)
<220> FEATURE:
<221> NAME/KEY: MISC_FEATURE
<222> LOCATION: (59)..(60)
<223> OTHER INFORMATION: Xaa59 = (Lys or Glu); Xaa60 = (Ala, Pro or Ser)
<220> FEATURE:
<221> NAME/KEY: MISC_FEATURE
<222> LOCATION: (65)..(72)
<223> OTHER INFORMATION: Xaa65 = (Thr or Glu); Xaa66 = (Glu, Gln or
      Lys); Xaa67 = (Leu or Met); Xaa68 = (Ser, Asn or Asp); Xaa69 =
      (Ala, Ser or Pro); Xaa70 = (Ile, Leu or Val); Xaa71 =
      (Ser or Ala); Xaa72 = (Met, Ile or Val)
```

-continued

<220> FEATURE:
<221> NAME/KEY: MISC_FEATURE
<222> LOCATION: (74)..(80)
<223> OTHER INFORMATION: Xaa74 = (Tyr or Phe); Xaa75 = (Leu, Phe or Tyr) ; Xaa76 = (Asp or Asn); Xaa77 = (Glu, Asp or Asn); Xaa78 = (Asn or Gln); Xaa79 = (Glu, Asp, Ser or Lys); Xaa80 = (Asn or Lys)
<220> FEATURE:
<221> NAME/KEY: MISC_FEATURE
<222> LOCATION: (82)..(82)
<223> OTHER INFORMATION: Xaa82 = (Val or Ile)
<220> FEATURE:
<221> NAME/KEY: MISC_FEATURE
<222> LOCATION: (84)..(85)
<223> OTHER INFORMATION: Xaa84 = (Lys or Arg); Xaa85 = (Asn, Lys or His)
<220> FEATURE:
<221> NAME/KEY: MISC_FEATURE
<222> LOCATION: (87)..(88)
<223> OTHER INFORMATION: Xaa87 = (Gln, Glu, Arg or Pro); Xaa88 = (Asp, Glu or Asn)
<220> FEATURE:
<221> NAME/KEY: MISC_FEATURE
<222> LOCATION: (90)..(90)
<223> OTHER INFORMATION: Xaa90 = (Val or Thr)
<220> FEATURE:
<221> NAME/KEY: MISC_FEATURE
<222> LOCATION: (92)..(93)
<223> OTHER INFORMATION: Xaa92 = (Glu, Asp or Arg); Xaa93 = (Gly, Ala, Ser or Glu)
<220> FEATURE:
<221> NAME/KEY: MISC_FEATURE
<222> LOCATION: (95)..(95)
<223> OTHER INFORMATION: Xaa95 = (Gly or His)
<220> FEATURE:
<221> NAME/KEY: MISC_FEATURE
<222> LOCATION: (97)..(97)
<223> OTHER INFORMATION: Xaa97 = (Arg or His)

<400> SEQUENCE: 13

```
Leu Xaa Val Xaa Phe Xaa Asp Xaa Gly Trp Xaa Xaa Trp Xaa Xaa Xaa
1               5                   10                  15

Pro Xaa Gly Xaa Xaa Ala Xaa Tyr Cys Xaa Gly Xaa Cys Xaa Xaa Pro
            20                  25                  30

Xaa Xaa Xaa Xaa Xaa Xaa Xaa Xaa Asn His Ala Xaa Xaa Gln Xaa Xaa
        35                  40                  45

Val Xaa Xaa Xaa Asn Xaa Xaa Xaa Xaa Pro Xaa Xaa Cys Cys Val Pro
    50                  55                  60

Xaa Xaa Xaa Xaa Xaa Xaa Xaa Xaa Leu Xaa Xaa Xaa Xaa Xaa Xaa Xaa
65                  70                  75                  80

Val Xaa Leu Xaa Xaa Tyr Xaa Xaa Met Xaa Val Xaa Xaa Cys Xaa Cys
                85                  90                  95

Xaa
```

<210> SEQ ID NO 14
<211> LENGTH: 102
<212> TYPE: PRT
<213> ORGANISM: Artificial Sequence
<220> FEATURE:
<223> OTHER INFORMATION: Description of Artificial Sequence: Generic amino acid sequence
<220> FEATURE:
<221> NAME/KEY: MISC_FEATURE
<222> LOCATION: (2)..(2)
<223> OTHER INFORMATION: Xaa2 = (Lys or Arg)
<220> FEATURE:
<221> NAME/KEY: MISC_FEATURE
<222> LOCATION: (4)..(5)
<223> OTHER INFORMATION: Xaa4 = (His, Arg, or Lys); Xaa5 = (Pro, Ser or Glu)
<220> FEATURE:
<221> NAME/KEY: MISC_FEATURE
<222> LOCATION: (7)..(7)

-continued

```
<223> OTHER INFORMATION: Xaa7 = (Tyr, Lys or Phe)
<220> FEATURE:
<221> NAME/KEY: MISC_FEATURE
<222> LOCATION: (9)..(9)
<223> OTHER INFORMATION: Xaa9 = (Asp, Ser or Glu)
<220> FEATURE:
<221> NAME/KEY: MISC_FEATURE
<222> LOCATION: (11)..(11)
<223> OTHER INFORMATION: Xaa11 = (Arg, Ser, Lys or Ala)
<220> FEATURE:
<221> NAME/KEY: MISC_FEATURE
<222> LOCATION: (13)..(13)
<223> OTHER INFORMATION: Xaa13 = (Val, Leu or Ile)
<220> FEATURE:
<221> NAME/KEY: MISC_FEATURE
<222> LOCATION: (16)..(17)
<223> OTHER INFORMATION: Xaa16 = (Asn, Gln, Asp or Ser); Xaa17 = (Asp,
      Glu or Asn)
<220> FEATURE:
<221> NAME/KEY: MISC_FEATURE
<222> LOCATION: (19)..(21)
<223> OTHER INFORMATION: Xaa19 = (Ile or Val); Xaa20 = (Val or Ile);
      Xaa 21 = (Ala or Ser)
<220> FEATURE:
<221> NAME/KEY: MISC_FEATURE
<222> LOCATION: (23)..(23)
<223> OTHER INFORMATION: Xaa23 = (Pro, Glu, Leu or Lys)
<220> FEATURE:
<221> NAME/KEY: MISC_FEATURE
<222> LOCATION: (25)..(26)
<223> OTHER INFORMATION: Xaa25 = (Tyr or Phe); Xaa26 = (His or Asp)
<220> FEATURE:
<221> NAME/KEY: MISC_FEATURE
<222> LOCATION: (28)..(28)
<223> OTHER INFORMATION: Xaa28 = (Phe, Tyr or Asn)
<220> FEATURE:
<221> NAME/KEY: MISC_FEATURE
<222> LOCATION: (31)..(31)
<223> OTHER INFORMATION: Xaa31 = (His, Glu or Ser)
<220> FEATURE:
<221> NAME/KEY: MISC_FEATURE
<222> LOCATION: (33)..(33)
<223> OTHER INFORMATION: Xaa33 = (Glu or Ala)
<220> FEATURE:
<221> NAME/KEY: MISC_FEATURE
<222> LOCATION: (35)..(36)
<223> OTHER INFORMATION: Xaa35 = (Pro, Ala or Gln); Xaa36 = (Phe or Tyr)
<220> FEATURE:
<221> NAME/KEY: MISC_FEATURE
<222> LOCATION: (38)..(45)
<223> OTHER INFORMATION: Xaa38 = (Leu, Met or Ile); Xaa39 = (Ala, Pro or
      Thr); Xaa40 = (Asp, Glu or Lys); Xaa41 = (His or Ser); Xaa42 =
      (Leu, Met or Phe); Xaa43 = (Asn or Lys); Xaa44 = (Ser, Ala or Pro)
      ; Xaa45 = (Thr or Ser)
<220> FEATURE:
<221> NAME/KEY: MISC_FEATURE
<222> LOCATION: (49)..(50)
<223> OTHER INFORMATION: Xaa49 = (Ile, Val or Thr); Xaa50 = (Val, Ile
      or Leu)
<220> FEATURE:
<221> NAME/KEY: MISC_FEATURE
<222> LOCATION: (52)..(53)
<223> OTHER INFORMATION: Xaa52 = (Thr or Ser); Xaa53 = (Leu or Ile)
<220> FEATURE:
<221> NAME/KEY: MISC_FEATURE
<222> LOCATION: (55)..(57)
<223> OTHER INFORMATION: Xaa55 = (Asn, His or Arg); Xaa56 = (Ser, Ala,
      Phe or Asn); Xaa57 = (Val or Ile)
<220> FEATURE:
<221> NAME/KEY: MISC_FEATURE
<222> LOCATION: (59)..(62)
<223> OTHER INFORMATION: Xaa59 = (Pro or Ser); Xaa60 = (Gly or Glu);
      Xaa61 = (Lys, Gln, Thr or Ser); Xaa62 = (Ile or Val)
<220> FEATURE:
<221> NAME/KEY: MISC_FEATURE
<222> LOCATION: (64)..(65)
<223> OTHER INFORMATION: Xaa64 = (Lys or Glu); Xaa65 = (Ala, Pro or Ser)
<220> FEATURE:
<221> NAME/KEY: MISC_FEATURE
```

-continued

```
<222> LOCATION: (70)..(77)
<223> OTHER INFORMATION: Xaa70 = (Thr or Glu); Xaa71 = (Glu, Gln or Lys)
      ; Xaa72 = (Leu or Met); Xaa73 = (Ser, Asn or Asp); Xaa74 =
      (Ala, Ser or Pro); Xaa75 = (Ile, Leu or Val); Xaa76 = (Ser or
      Ala); Xaa77 = (Met, Ile or Val)
<220> FEATURE:
<221> NAME/KEY: MISC_FEATURE
<222> LOCATION: (79)..(85)
<223> OTHER INFORMATION: Xaa79 = (Tyr or Phe); Xaa80 = (Leu, Phe or Tyr)
      ; Xaa81 = (Asp or Asn); Xaa82 = (Glu, Asp or Asn); Xaa83 = (Asn or
      Gln); Xaa84 = (Glu, Asp, Ser or Lys); Xaa85 = (Asn or Lys)
<220> FEATURE:
<221> NAME/KEY: MISC_FEATURE
<222> LOCATION: (87)..(87)
<223> OTHER INFORMATION: Xaa87 = (Val or Ile)
<220> FEATURE:
<221> NAME/KEY: MISC_FEATURE
<222> LOCATION: (89)..(90)
<223> OTHER INFORMATION: Xaa89 = (Lys or Arg); Xaa90 = (Asn, Lys or His)
<220> FEATURE:
<221> NAME/KEY: MISC_FEATURE
<222> LOCATION: (92)..(93)
<223> OTHER INFORMATION: Xaa92 = (Gln, Glu, Arg or Pro); Xaa93 = (Asp,
      Glu or Asn)
<220> FEATURE:
<221> NAME/KEY: MISC_FEATURE
<222> LOCATION: (95)..(95)
<223> OTHER INFORMATION: Xaa95 = (Val or Thr)
<220> FEATURE:
<221> NAME/KEY: MISC_FEATURE
<222> LOCATION: (97)..(98)
<223> OTHER INFORMATION: Xaa97 = (Glu, Asp or Arg); Xaa98 = (Gly, Ala,
      Ser or Glu)
<220> FEATURE:
<221> NAME/KEY: MISC_FEATURE
<222> LOCATION: (100)..(100)
<223> OTHER INFORMATION: Xaa100 = (Gly or His)
<220> FEATURE:
<221> NAME/KEY: MISC_FEATURE
<222> LOCATION: (102)..(102)
<223> OTHER INFORMATION: Xaa102 = (Arg or His)

<400> SEQUENCE: 14

Cys Xaa Arg Xaa Xaa Leu Xaa Val Xaa Phe Xaa Asp Xaa Gly Trp Xaa
1               5                   10                  15

Xaa Trp Xaa Xaa Xaa Pro Xaa Gly Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

Xaa Xaa Gln Xaa Xaa Val Xaa Xaa Xaa Asn Xaa Xaa Xaa Xaa Pro Xaa
    50                  55                  60

Xaa Cys Cys Val Pro Xaa Xaa Xaa Xaa Xaa Xaa Xaa Xaa Leu Xaa Xaa
65                  70                  75                  80

Xaa Xaa Xaa Xaa Xaa Val Xaa Leu Xaa Xaa Tyr Xaa Xaa Met Xaa Val
                85                  90                  95

Xaa Xaa Cys Xaa Cys Xaa
            100
```

COMPOSITIONS AND THERAPEUTIC METHODS USING MORPHOGENIC PROTEINS, HORMONES AND HORMONE RECEPTORS

CROSS REFERENCE TO RELATED APPLICATION

Under 35 U.S.C. §119(e)(1), this application claims the benefit of prior U.S. provisional application serial No. 60/156,261, filed Sep. 27, 1999.

BACKGROUND OF THE INVENTION

The Transforming Growth Factor-Beta ("TGF-β") superfamily represents a large number of evolutionarily conserved morphogenic proteins with diverse activities in growth, differentiation, tissue morphogenesis and repair. This superfamily includes osteogenic proteins ("OPs") and bone morphogenic proteins ("BMPs"). OPs and BMPs share a highly conserved, bioactive cysteine-rich domain near their C-termini and have a propensity to form homo- and hetero-dimers.

Many morphogenic proteins belonging to the BMP family have been described. Some were isolated using purification techniques on the basis of osteogenic activity. Others were identified and cloned by virtue of DNA sequence homologies within conserved regions that are common to the BMP family. These homologs are referred to as consecutively numbered BMPs whether or not they have demonstrable osteogenic activity. While several of the earliest members of the BMP family were identified by virtue of their ability to induce new cartilage and bone, a number of other BMPs have different or additional tissue-inductive capabilities. For example, BMP-12 and BMP-13 (identified by DNA sequence homology) reportedly induce tendon/ligament-like tissue formation in vivo (WO 95/16035). Several BMPs, including some of those originally isolated on the basis of their osteogenic activity, can induce neuron proliferation and promote axon regeneration (WO 95/05846; Liem et al., *Cell*, 82, pp. 969–79 (1995)). Thus, it appears that BMPs may have a variety of potential tissue-inductive capabilities whose final expression depends on a complex set of developmental and environmental cues.

Many of the mammalian BMPs have been recombinantly expressed as active homo- or heterodimers in a variety of host systems, making therapeutic treatments using morphogenic proteins feasible. Implantable osteogenic devices comprising mammalian osteogenic protein for promoting bone healing and regeneration have been described (see, e.g., Oppermann et al., U.S. Pat. No. 5,354,557). Some osteogenic devices contain porous, biocompatible matrices that allow the diffusion of osteogenic proteins into the implantation site as well as the influx and efflux of progenitor cells. Osteogenic protein-coated prosthetic devices that enhance the bond strength between the prosthesis and existing bone have also been described (Rueger et al., U.S. Pat. No. 5,344,654).

SUMMARY OF THE INVENTION

This invention is based on the discovery that the tissue-inductive activity of a morphogenic protein can be enhanced by a hormone in the presence of a soluble receptor of the hormone.

Accordingly, this invention features a method for improving the tissue inductive capability of a morphogenic protein at a target locus in a mammal. In this method, the morphogenic protein and a first effective amount of a hormone and a second effective amount of a soluble receptor of the hormone are administered to the target locus, wherein the morphogenic protein is capable of inducing tissue formation when accessible to a progenitor cell in the mammal, and the hormone and the receptor in combination enhance that capability. The morphogenic protein, hormone and hormone receptor can be administered simultaneously to the target locus. Alternatively, the three components are administered separately, in any order: for instance, the morphogenic protein can be administered first, and then the hormone and hormone receptor are administered together; or the morphogenic protein and the hormone are administered together first, and then the hormone receptor is administered. In one embodiment, the morphogenic protein is administered via a nucleic acid (e.g., a plasmid, a viral vector, or naked DNA) that comprises a sequence encoding the morphogenic protein and is capable of expressing the morphogenic protein in the appropriate progenitor cells of a patient.

The morphogenic protein may comprise a pair of subunits disulfide-bonded to produce a dimeric species, wherein at least one of the subunits comprises a polypeptide belonging to the BMP protein family. For instance, the morphogenic protein may comprise an amino acid sequence sufficiently duplicative of the amino acid sequence of a reference BMP such as BMP-2, BMP-3, BMP-4, BMP-5, BMP-6, BMP-7 (OP-1), BMP-8, BMP-9, BMP-10, BMP-11, BMP-12, BMP-13, COP-5, or COP-7, such that it has morphogenic activity similar to that of the reference BMP. In one preferred embodiment, the morphogenic protein is a homo- or heterodimer comprising a BMP-2 or BMP-7 (OP-1) subunit.

The morphogenic protein is capable of inducing tissue formation. For instance, it may be capable of inducing the progenitor cell to form tissue tendon/ligament-like or neural-like tissue; or it may be an osteogenic protein that is capable of inducing the progenitor cell to form endochondral or intramembranous bone, or cartilage. The method of this invention thus can be used to induce tissue regeneration or repair in a variety of tissue defects such as bone, cartilage, soft tissue and neural tissue defects.

Hormones useful in this invention include but are not limited to cytokines (e.g., interleukins 1 through 18), growth factors (e.g., fibroblast growth factor, vascular endothelial growth factor, platelet-derived growth factor, TGF-β, or prostaglandin) or morphogenic proteins.

The invention also features pharmaceutical compositions and kits comprising a hormone and a soluble receptor thereof for improving the tissue inductive activity of a morphogenic protein. This invention also provides implantable morphogenic devices for inducing tissue formation in allogeneic and xenogeneic implants. Such devices comprise a morphogenic protein, a hormone and a soluble receptor thereof disposed within a carrier. Methods for inducing local tissue formation from a progenitor cell in a mammal using those compositions and devices are also provided. A method for accelerating allograft repair in a mammal using those morphogenic devices is provided. This invention also provides a prosthetic device comprising a prosthesis coated with a morphogenic protein, a hormone and a soluble receptor thereof, and a method for promoting in vivo integration of an implantable prosthetic device to enhance the bond strength between the prosthesis and the existing target tissue at the joining site. Methods for treating tissue degenerative conditions in a mammal using the pharmaceutical compositions are also provided.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting.

Other features and advantages of the invention will be apparent from the following drawings, detailed description, and the claims.

DETAILED DESCRIPTION OF THE INVENTION

Figure 1:
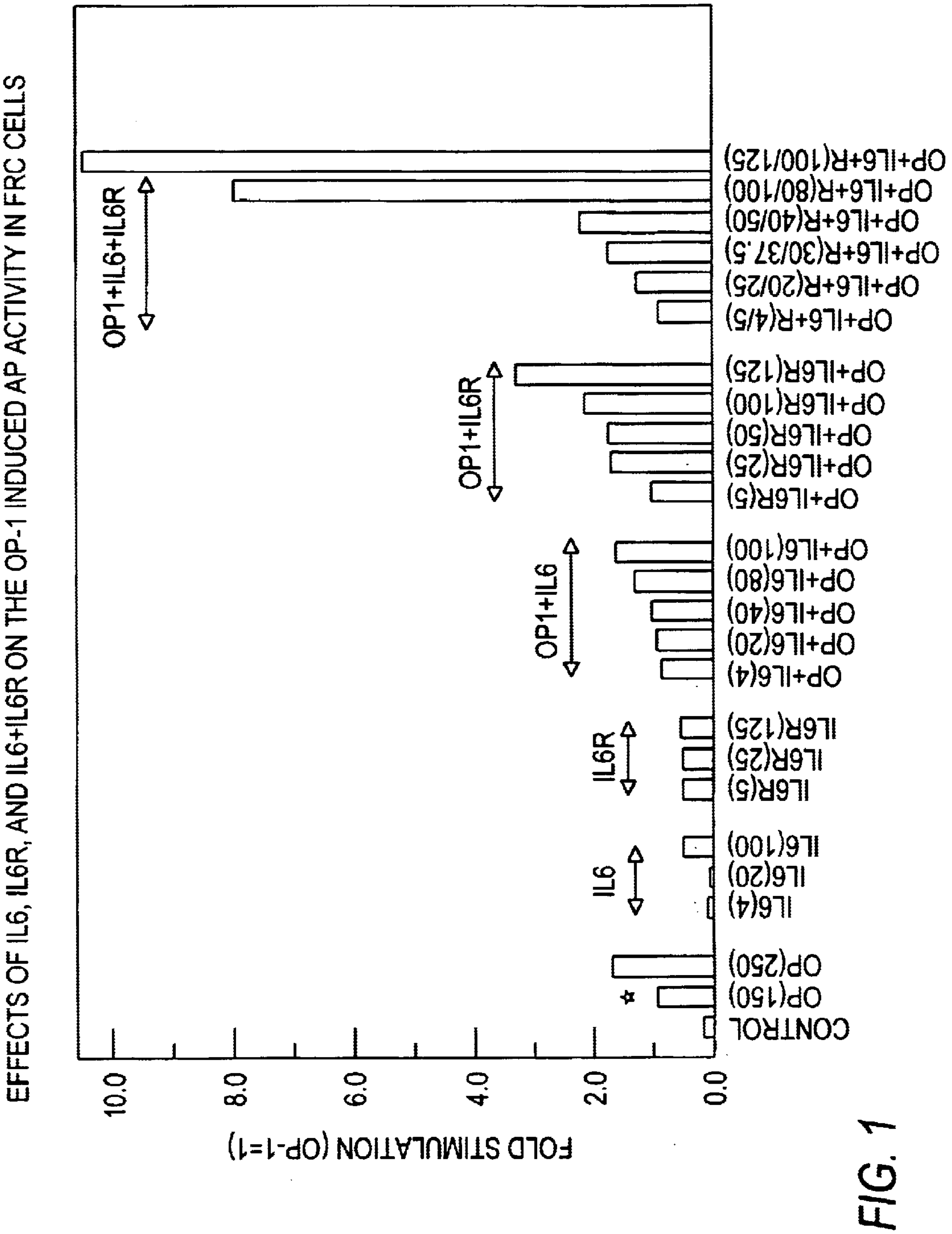
FIG. 1 is a bar graph showing that a combination of interleukin 6 ("IL-6") and soluble IL-6 receptor ("sIL-6R") significantly increases the ability of OP-1 to induce alkaline phosphatase ("AP") activity in fetal rat calvaria ("FRC") cells. "OP" stands for "OP-1"; "IL-6R" refers to "sIL-6R." The parenthesized numbers indicate the protein concentrations (ng/ml) used in the assay; in the case of IL-6/sIL-6R combinations, the two numbers separated by a backslash in the parenthesis indicate the protein concentrations of IL-6 and sIL-6R, respectively.

In order that the invention herein described may be fully understood, the following detailed description is set forth.

The term "biocompatible" refers to a material that does not elicit detrimental effects associated with the body's various protective systems, such as cell and humoral-associated immune responses, e.g., inflammatory responses and foreign body fibrotic responses. This term also implies that no specific undesirable effects, cytotoxic or systemic, are caused by the material when it is implanted into the patient.

The term "BMP" refers to a protein belonging to the BMP family of the TGF-β superfamily of proteins defined on the basis of DNA and amino acid sequence homology. According to this invention, a protein belongs to the BMP family when it has at least 50% (e.g., at least 70% or even 85%) amino acid sequence homology with a known BMP family member within the conserved C-terminal cysteine-rich domain that characterizes the BMP family. Members of the BMP family may have less than 50% DNA or amino acid sequence homology overall.

The term "morphogenic protein" refers to a protein having morphogenic activity. For instance, this protein is capable of inducing progenitor cells to proliferate and/or to initiate differentiation pathways that lead to the formation of cartilage, bone, tendon, ligament, neural or other types of tissue, depending on local environmental cues. Thus, morphogenic proteins useful in this invention may behave differently in different surroundings. A morphogenic protein of this invention may comprise at least one polypeptide belonging to the BMP family.

The term "osteogenic protein" refers to a morphogenic protein that is capable of inducing a progenitor cell to form cartilage and/or bone. The bone may be intramembranous bone or endochondral bone. Most osteogenic proteins are members of the BMP family and are thus also BMPs. However, the converse may not be true. According to this invention, a BMP identified by sequence homology must have demonstrable osteogenic or chondrogenic activity in a functional bioassay to be an osteogenic protein.

The terms "morphogenic activity," "inducing activity" and "tissue inductive activity" alternatively refer to the ability of an agent to stimulate a target cell to undergo one or more cell divisions (proliferation) that may optionally lead to cell differentiation. Such target cells are referred to generically herein as progenitor cells. Cell proliferation is typically characterized by changes in cell cycle regulation and may be detected by a number of means which include measuring DNA synthetic or cellular growth rates. Early stages of cell differentiation are typically characterized by changes in gene expression patterns relative to those of the progenitor cell; such changes may be indicative of a commitment towards a particular cell fate or cell type. Later stages of cell differentiation may be characterized by changes in gene expression patterns, cell physiology and morphology. Any reproducible change in gene expression, cell physiology or morphology may be used to assess the initiation and extent of cell differentiation induced by a morphogenic protein.

The term "synergistic interaction" refers to an interaction in which the combined effect of two or more agents is greater than the algebraic sum of their individual effects.

The term "hormone/receptor pair" refers to a combination of a hormone and a soluble receptor thereof. The hormone (e.g., a cytokine, a growth factor, or a morphogenic protein) can be of any mammalian origin (e.g., human, bovine, or murine). A soluble receptor of a hormone is a compound that binds specifically to the hormone, and can, for example, be a polypeptide containing only the hormone-binding domain (e.g., an extracellular domain) of a native cellular receptor of the hormone, an antibody specific for the hormone, or a chemical compound that specifically interacts with the hormone. A soluble receptor can also be a compound (e.g., a protein) containing a domain that specifically binds to the hormone and another domain that specifically binds to the native cellular receptor of the hormone such that the soluble receptor facilitates the binding of the hormone to its native cellular receptor; an example of such a soluble receptor is the IGF-binding protein.

Morphogenic Proteins

The morphogenic proteins of this invention are capable of stimulating a progenitor cell to undergo cell division and/or differentiation. They may belong to the TGF-β protein superfamily, and include, but are not limited to, OP-1, OP-2, OP-3, BMP-2, BMP-3, BMP-3b, BMP-4, BMP-5, BMP-6, BMP-9, BMP-10, BMP-11, BMP-12, BMP-13, BMP-14, BMP-15, GDF-1, GDF-2, GDF-3, GDF-5, GDF-6, GDF-7, GDF-8, GDF-9, GDF-10, GDF-11, GDF-12, DPP, Vg-1, Vgr-1, 60A protein, NODAL, UNIVIN, SCREW, ADMP, NEURAL, and TGF-β.

One of the preferred morphogenic proteins is OP-1. Nucleotide and amino acid sequences for hOP-1 are provided in SEQ ID NOs:1 and 2, respectively. For ease of description, hOP-1 is recited as a representative morphogenic protein. It will be appreciated by the ordinarily skilled artisan that OP-1 is merely representative of a family of morphogens.

Other useful morphogenic proteins also include polypeptides having at least 50% (e.g., at least 70% or even 85%) sequence homology with a known morphogenic protein, particularly with a known BMP within the conserved C-terminal cysteine-rich domain that characterizes the BMP protein family. These morphogenic proteins include biologically active variants of any known morphogenic protein, including variants containing conservative amino acid changes. For instance, useful morphogenic proteins include those containing sequences that share at least 70% amino acid sequence homology with the C-terminal seven-cysteine domain of hOP-1, which domain corresponds to the C-terminal 102–106 amino acid residues of SEQ ID NO:2. The C-terminal 102 amino acid residues corresponds to residues 330–431 of SEQ ID NO:2. In one embodiment of this invention, the morphogenic protein consists of a pair of subunits disulfide-bonded to produce a dimer, wherein at least one of the subunits comprises a recombinant polypeptide belonging to the BMP family.

As used herein, "amino acid sequence homology" is understood to include both amino acid sequence identity and similarity. Homologous sequences share identical and/or similar amino acid residues, where similar residues are conservative substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. Certain particularly preferred morphogenic polypeptides share at least 60% (e.g., at least 65%) amino acid sequence identity with the C-terminal seven-cysteine domain of human OP-1.

As used herein, "conservative substitutions" are residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., *Atlas of Protein Sequence and Structure* 5:345–352 (1978 & Supp.). Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine. The term "conservative variant" or "conservative variation" also includes the use of a substituting amino acid residue in place of an amino acid residue in a given parent amino acid sequence, where antibodies specific for the parent sequence are also specific for, i.e., "cross-react" or "immuno-react" with, the resulting substituted polypeptide sequence.

Amino acid sequence homology can be determined by methods well known in the art. For instance, to determine the percent homology of a candidate amino acid sequence to the sequence of the seven-cysteine domain, the two sequences are first aligned. The alignment can be made with, e.g., the dynamic programming algorithm described in Needleman et al., *J. Mol. Biol.* 48:443 (1970), and the Align Program, a commercial software package produced by DNAstar, Inc. The teachings by both sources are incorporated by reference herein. An initial alignment can be refined by comparison to a multi-sequence alignment of a family of related proteins. Once the alignment is made and refined, a percent homology score is calculated. The aligned amino acid residues of the two sequences are compared sequentially for their similarity to each other. Similarity factors include similar size, shape and electrical charge. One particularly preferred method of determining amino acid similarities is the PAM250 matrix described in Dayhoff et al., supra. A similarity score is first calculated as the sum of the aligned pairwise amino acid similarity scores. Insertions and deletions are ignored for the purposes of percent homology and identity. Accordingly, gap penalties are not used in this calculation. The raw score is then normalized by dividing it by the geometric mean of the scores of the candidate sequence and the seven-cysteine domain. The geometric mean is the square root of the product of these scores. The normalized raw score is the percent homology.

Morphogenic proteins useful herein include any known naturally occurring native proteins, including allelic, phylogenetic counterparts and other variants thereof. These variants include forms having varying glycosylation patterns, varying N-termini, and active truncated or mutated forms of a native protein. Useful morphogenic proteins also include those that are biosynthetically produced (e.g., "muteins" or "mutant proteins") and those that are new, morphogenically active members of the general morphogenic family of proteins. Particularly useful sequences include those comprising the C-terminal 96 to 102 amino acid residues of: DPP (from Drosophila), Vg-1 (from Xenopus), Vgr-1 (from mouse), the OP1 and OP2 proteins (U.S. Pat. No. 5,011,691), as well as the proteins referred to as BMP-2, BMP-3, BMP-4 (WO 88/00205, U.S. Pat. No. 5,013,649 and WO 91/18098), BMP-5 and BMP-6 (WO 90/11366), BMP-8 and BMP-9. Other proteins useful in the practice of the invention include active forms of OP1, OP2, OP3, BMP-2, BMP-3, BMP-3b, BMP-4, BMP-5, BMP-6, BMP-9, BMP-10, BMP-11, BMP-12, BMP-13, BMP-14, BMP-15, DPP, Vg-1, Vgr-1, 60A protein, GDF-1, GDF-2, GDF-3, GDF-5, GDF-6, GDF-7, GDF-8, GDF-9, and GDF-10, GDF-11, GDF-12, GDF-13, UNIVIN, NODAL, SCREW, ADMP, NEURAL, and TGF-β.

Osteogenic proteins useful as morphogenic proteins of this invention include those containing sequences that share greater than 60% identity with the seven-cysteine domain. In other embodiments, useful osteogenic proteins are defined as osteogenically active proteins having any one of the generic sequences defined herein, including OPX (SEQ ID NO:3) and Generic Sequences 7 (SEQ ID NO:4), 8 (SEQ ID NO:5), 9 (SEQ ID NO:6) and 10 (SEQ ID NO:7).

Generic Sequence 7 (SEQ ID NO:4) and Generic Sequence 8 (SEQ ID NO:5), disclosed below, accommodate the homologies shared among preferred protein family members identified to date, including OP-1, OP-2, OP-3, BMP-2, BMP-3, BMP-4, BMP-5, BMP-6, 60A, DPP, Vg-1, Vgr-1, and GDF-1. The amino acid sequences for these proteins are described herein and/or in the art. The generic sequences include the identical amino acid residues shared by these sequences in the C-terminal six- or seven-cysteine skeletal domains (represented by Generic Sequences 7 and 8, respectively), as well as alternative residues for the variable positions within the sequences. The generic sequences provide an appropriate cysteine skeleton where inter- or intra-molecular disulfide bonds can form. Those sequences contain certain specified amino acids that may influence the tertiary structure of the folded proteins. In addition, the generic sequences allow for an additional cysteine at position 36 (Generic Sequence 7) or position 41 (Generic Sequence 8), thereby encompassing the biologically active sequences of OP-2 and OP-3.

Xaa at res.56=(Thr, Ala, Val, Lys, Asp, Tyr, Ser, Gly, Ile or His); Xaa at res.57=(Val, Ala or Ile); Xaa at res.58=(Pro or Asp); Xaa at res.59=(Lys, Leu or Glu); Xaa at res.60=(Pro, Val or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Leu, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn, Arg or Ser); Xaa at res.78=(Ser, Gln, Asn, Tyr or Asp); Xaa at res.79=(Ser,

GENERIC SEQUENCE 7

```
        Leu Xaa Xaa Xaa Phe Xaa Xaa Xaa Gly Trp Xaa Xaa Xaa Xaa Xaa Xaa   (SEQ ID NO:4)
         1               5                   10                  15

Pro Xaa Xaa Xaa Xaa Ala Xaa Tyr Cys Xaa Gly Xaa Cys Xaa Xaa Pro Xaa Xaa
            20                  25                   30

Xaa Xaa Xaa Xaa Xaa Xaa Asn His Ala Xaa Xaa Xaa Xaa Xaa Xaa Xaa Xaa Xaa
35                  40                  45                  50

Xaa Xaa Xaa Xaa Xaa Xaa Xaa Xaa Cys Cys Xaa Pro Xaa Xaa Xaa Xaa Xaa Xaa
        55                  60                  65                   70

Xaa Xaa Leu Xaa Xaa Xaa Xaa Xaa Xaa Xaa Val Xaa Leu Xaa Xaa Xaa Xaa Xaa
                75                         80                  85

Met Xaa Val Xaa Xaa Cys Xaa Cys Xaa
    90                  95
```

wherein each Xaa is independently defined as follows ("Res." means "residue"): Xaa at res.2=(Tyr or Lys); Xaa at res.3=(Val or Ile); Xaa at res.4=(Ser, Asp or Glu); Xaa at res.6=(Arg, Gln, Ser, Lys or Ala); Xaa at res.7=(Asp or Glu); Xaa at res.8=(Leu, Val or Ile); Xaa at res.11=(Gln, Leu, Asp, His, Asn or Ser); Xaa at res.12=(Asp, Arg, Asn or Glu); Xaa at res.13=(Trp or Ser); Xaa at res.14=(Ile or Val); Xaa at res.5=(Ile or Val); Xaa at res.16 (Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln, Ala or Ser); Xaa at res.28=(Glu, Lys, Asp, Gln or Ala); Xaa at res.30=(Ala, Ser, Pro, Gln, Ile or Asn); Xaa at res.31=(Phe, Leu or Tyr); Xaa at res.33=(Leu, Val or Met); Xaa at res.34=(Asn, Asp, Ala, Thr or Pro); Xaa at res.35=(Ser, Asp, Glu, Leu, Ala or Lys); Xaa at res.36=(Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu, Met or Ile); Xaa at res.46=(Gln or Arg); Xaa at res.47=(Thr, Ala or Ser); Xaa at res.48 =(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val, Gly or Leu); Xaa at res.53=(Asn, Lys, Ala, Glu, Gly or Phe); Xaa at res.54=(Pro, Ser or Val); Xaa at res.55=(Glu, Asp, Asn, Gly, Val, Pro or Lys); Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His, Arg or Val); Xaa at res.86=(Tyr, Glu or His); Xaa at res.87=(Arg, Gln, Glu or Pro); Xaa at res.88=(Asn, Glu, Trp or Asp); Xaa at res.90=(Val, Thr, Ala or Ile); Xaa at res.92=(Arg, Lys, Val, Asp, Gln or Glu); Xaa at res.93=(Ala, Gly, Glu or Ser); Xaa at res.95=(Gly or Ala); and Xaa at res.97=(His or Arg).

Generic Sequence 8 (SEQ ID NO:5) includes all of Generic Sequence 7 and in addition includes the following five amino acid at its N-terminus: Cys Xaa Xaa Xaa Xaa (SEQ ID NO:8), wherein Xaa at res.2=(Lys, Arg, Ala or Gln); Xaa at res.3=(Lys, Arg or Met); Xaa at res.4=(His, Arg or Gln); and Xaa at res.5=(Glu, Ser, His, Gly, Arg, Pro, Thr, or Tyr). Accordingly, beginning with residue 7, each "Xaa" in Generic Sequence 8 is a specified amino acid as defined as for Generic Sequence 7, with the distinction that each residue number described for Generic Sequence 7 is shifted by five in Generic Sequence 8. For example, "Xaa at res.2=(Tyr or Lys)" in Generic Sequence 7 corresponds to Xaa at res.7 in Generic Sequence 8.

Generic Sequences 9 (SEQ ID NO:6) and 10 (SEQ ID NO:7) are composite amino acid sequences of the following proteins: human OP-1 ("hOP-1"), hOP-2, hOP-3, hBMP-2, hBMP-3, hBMP-4, hBMP-5, hBMP-6, hBMP-9, hBMP10, hBMP-11, Drosophila 60A, Xenopus Vg-1, sea urchin UNIVIN, hCDMP-1 (mouse GDF-5 or "mGDF-5"), hCDMP-2 (mGDF-6, hBMP-13), hCDMP-3 (mGDF-7, hBMP-12), mGDF-3, hGDF-1, mGDF-1, chicken DORSALIN, DPP, Drosophila SCREW, mouse NODAL, mGDF-8, hGDF-8, mGDF-9, mGDF-10, hGDF-11, mGDF-11, hBMP-15, and rat BMP3b. Like Generic Sequence 7, Generic Sequence 9 accommodates the C-terminal six-cysteine skeleton and, like Generic Sequence 8, Generic Sequence 10 accommodates the C-terminal seven-cysteine skeleton.

Val, Thr or Gln); Xaa at res.42=(His, Tyr or Lys); Xaa at res.43=(Ala, Thr, Leu or Tyr); Xaa at res.44=(Ile, Thr, Val, Phe, Tyr, Met or Pro); Xaa at res.45=(Val, Leu, Met, Ile or His); Xaa at res.46=(Gln, Arg or Thr); Xaa at res.47=(Thr, Ser, Ala, Asn or His); Xaa at res.48=(Leu, Asn or Ile); Xaa at res.49=(Val, Met, Leu, Pro or Ile); Xaa at res.50=(His, Asn, Arg, Lys, Tyr or Gln); Xaa at res.51=(Phe, Leu, Ser, Asn, Met, Ala, Arg, Glu, Gly or Gln); Xaa at res.52=(Ile, Met, Leu, Val, Lys, Gln, Ala or Tyr); Xaa at res.53=(Asn,

GENERIC SEQUENCE 9

```
          Xaa Xaa Xaa Xaa Xaa Xaa Xaa Xaa Xaa Xaa Xaa Xaa Xaa Xaa Xaa Xaa  (SEQ ID NO:6)
          1               5                   10                  15

Pro Xaa Xaa Xaa Xaa Xaa Xaa Xaa Cys Xaa Gly Xaa Cys Xaa Xaa Xaa Xaa
         20                  25                  30

Xaa Xaa Xaa Xaa Xaa Xaa Xaa Xaa Xaa Xaa Xaa Xaa Xaa Xaa Xaa Xaa Xaa
     35                  40                  45                  50

Xaa Xaa Xaa Xaa Xaa Xaa Xaa Xaa Xaa Xaa Xaa Cys Xaa Pro Xaa Xaa Xaa
                 55                  60                      65

Xaa Xaa Xaa Xaa Xaa Leu Xaa Xaa Xaa Xaa Xaa Xaa Xaa Xaa Xaa Xaa Xaa
         70                  75                  80

Xaa Xaa Xaa Xaa Xaa Xaa Xaa Xaa Xaa Cys Xaa Cys Xaa
85                  90                  95
```

wherein each Xaa is independently defined as follows: Xaa at res.1=(Phe, Leu or Glu), Xaa at res.2=(Tyr, Phe, His, Arg, Thr, Lys, Gln, Val or Glu); Xaa at res.3=(Val, Ile, Leu or Asp); Xaa at res.4=(Ser, Asp, Glu, Asn or Phe); Xaa at res.5=(Phe or Glu); Xaa at res.6 (Arg, Gln, Lys, Ser, Glu, Ala or Asn); Xaa at res.7=(Asp, Glu, Leu, Ala or Gln); Xaa at res.8=(Leu, Val, Met, Ile or Phe); Xaa at res.9=(Gly, His or Lys); Xaa at res.10=(Trp or Met); Xaa at res.11=(Gln, Leu, His, Glu, Asn, Asp, Ser or Gly); Xaa at res.12=(Asp, Asn, Ser, Lys, Arg, Glu or His); Xaa at res.13=(Trp or Ser); Xaa at res.14=(Ile or Val); Xaa at res.15=(Ile or Val); Xaa at res.16=(Ala, Ser, Tyr or Trp); Xaa at res.18=(Glu, Lys, Gln, Met, Pro, Leu, Arg, His or Lys); Xaa at res.19=(Gly, Glu, Asp, Lys, Ser, Gln, Arg or Phe); Xaa at res.20=(Tyr or Phe); Xaa at res.21=(Ala, Ser, Gly, Met, Gln, His, Glu, Asp, Leu, Asn, Lys or Thr); Xaa at res.22=(Ala or Pro); Xaa at res.23=(Tyr, Phe, Asn, Ala or Arg); Xaa at res.24=(Tyr, His, Glu, Phe or Arg); Xaa at res.26=(Glu, Asp, Ala, Ser, Tyr, His, Lys, Arg, Gln or Gly); Xaa at res.28=(Glu, Asp, Leu, Val, Lys, Gly, Thr, Ala or Gln); Xaa at res.30=(Ala, Ser, Ile, Asn, Pro, Glu, Asp, Phe, Gln or Leu); Xaa at res.31=(Phe, Tyr, Leu, Asn, Gly or Arg); Xaa at res.32=(Pro, Ser, Ala or Val); Xaa at res.33=(Leu, Met, Glu, Phe or Val); Xaa at res.34=(Asn, Asp, Thr, Gly, Ala, Arg, Leu or Pro); Xaa at res.35=(Ser, Ala, Glu, Asp, Thr, Leu, Lys, Gln or His); Xaa at res.36=(Tyr, His, Cys, Ile, Arg, Asp, Asn, Lys, Ser, Glu or Gly); Xaa at res.37=(Met, Leu, Phe, Val, Gly or Tyr); Xaa at res.38=(Asn, Glu, Thr, Pro, Lys, His, Gly, Met, Val or Arg); Xaa at res.39=(Ala, Ser, Gly, Pro or Phe); Xaa at res.40=(Thr, Ser, Leu, Pro, His or Met); Xaa at res.41=(Asn, Lys, Phe, Lys, Glu, Asp, Ala, Gln, Gly, Leu or Val); Xaa at res.54=(Pro, Asn, Ser, Val or Asp); Xaa at res.55=(Glu, Asp, Asn, Lys, Arg, Ser, Gly, Thr, Gln, Pro or His); Xaa at res.56=(Thr, His, Tyr, Ala, Ile, Lys, Asp, Ser, Gly or Arg); Xaa at res.57=(Val, Ile, Thr, Ala, Leu or Ser); Xaa at res.58=(Pro, Gly, Ser, Asp or Ala); Xaa at res.59=(Lys, Leu, Pro, Ala, Ser, Glu, Arg or Gly); Xaa at res.60=(Pro, Ala, Val, Thr or Ser); Xaa at res.61=(Cys, Val or Ser); Xaa at res.63=(Ala, Val or Thr); Xaa at res.65=(Thr, Ala, Glu, Val, Gly, Asp or Tyr); Xaa at res.66=(Gln, Lys, Glu, Arg or Val); Xaa at res.67=(Leu, Met, Thr or Tyr); Xaa at res.68=(Asn, Ser, Gly, Thr, Asp, Glu, Lys or Val); Xaa at res.69=(Ala, Pro, Gly or Ser); Xaa at res.70=(Ile, Thr, Leu or Val); Xaa at res.71=(Ser, Pro, Ala, Thr, Asn or Gly); Xaa at res.72=(Val, Ile, Leu or Met); Xaa at res.74=(Tyr, Phe, Arg, Thr, Tyr or Met); Xaa at res.75=(Phe, Tyr, His, Leu, Ile, Lys, Gln or Val); Xaa at res.76=(Asp, Leu, Asn or Glu); Xaa at res.77=(Asp, Ser, Arg, Asn, Glu, Ala, Lys, Gly or Pro); Xaa at res.78=(Ser, Asn, Asp, Tyr, Ala, Gly, Gln, Met, Glu, Asn or Lys); Xaa at res.79=(Ser, Asn, Glu, Asp, Val, Lys, Gly, Gln or Arg); Xaa at res.80=(Asn, Lys, Thr, Pro, Val, Ile, Arg, Ser or Gln); Xaa at res.81=(Val, Ile, Thr or Ala); Xaa at res.82=(Ile, Asn, Val, Leu, Tyr, Asp or Ala); Xaa at res.83=(Leu, Tyr, Lys or Ile); Xaa at res.84=(Lys, Arg, Asn, Tyr, Phe, Thr, Glu or Gly); Xaa at res.85=(Lys, Arg, His, Gln, Asn, Glu or Val); Xaa at res.86=(Tyr, His, Glu or Ile); Xaa at res.87=(Arg, Glu, Gln, Pro or Lys); Xaa at res.88=(Asn, Asp, Ala, Glu, Gly or Lys); Xaa at res.89=(Met or Ala); Xaa at res.90=(Val, Ile, Ala, Thr, Ser or Lys); Xaa at res.91=(Val or Ala); Xaa at res.92=(Arg, Lys, Gln, Asp, Glu, Val, Ala, Ser or Thr); Xaa at res.93=(Ala, Ser, Glu, Gly, Arg or Thr); Xaa at res.95=(Gly, Ala or Thr); and Xaa at res.97=(His, Arg, Gly, Leu or Ser). Further, after res.53 in rat BMP3b and mGDF-10 there is an Ile, after res.54 in GDF-1 there is a Thr; after res.54 in BMP3 there is a Val; after res.78 in BMP-8 and DORSALIN there is a Gly; after res.37 in hGDF-1 there are Pro, Gly, Gly, and Pro.

Generic Sequence 10 (SEQ ID NO:7) includes all of Generic Sequence 9 and in addition includes the following five amino acid residues at its N-terminus: Cys Xaa Xaa Xaa Xaa (SEQ ID NO:9), wherein Xaa at res.2=(Lys, Arg, Gln, Ser, His, Glu, Ala, or Cys); Xaa at res.3=(Lys, Arg, Met, Lys, Thr, Leu, Tyr, or Ala); Xaa at res.4=(His, Gln, Arg, Lys, Thr, Leu, Val, Pro, or Tyr); and Xaa at res.5=(Gln, Thr, His, Arg, Pro, Ser, Ala, Gln, Asn, Tyr, Lys, Asp, or Leu). Accordingly, beginning at res.6, each "Xaa" in Generic Sequence 10 is a specified amino acid defined as for Generic Sequence 9, with the distinction that each residue number described for Generic Sequence 9 is shifted by five in Generic Sequence 10. For example, "Xaa at res.1=(Phe, Leu or Glu)" in Generic Sequence 9 corresponds to Xaa at res.6 in Generic Sequence 10.

As noted above, certain preferred bone morphogenic proteins useful in this invention have greater than 60%, preferably greater than 65%, identity with the C-terminal seven-cysteine domain of hOP-1. These particularly preferred sequences include allelic and phylogenetic variants of the OP-1 and OP-2 proteins, including the Drosophila 60A protein. Accordingly, in certain particularly preferred embodiments, useful proteins include active proteins comprising dimers having the generic amino acid sequence "OPX" (SEQ ID NO:3), which defines the seven-cysteine skeleton and accommodates the homologies between several identified variants of OP-1 and OP-2. Each Xaa in OPX is independently selected from the residues occurring at the corresponding position in the C-terminal sequence of mouse or human OP-1 or OP-2.

```
                                   OPX

Cys Xaa Xaa His Glu Leu Tyr Val Ser Phe Xaa Asp Leu Gly Trp Xaa Asp Trp  (SEQ ID NO:3)
1               5                   10                  15

Xaa Ile Ala Pro Xaa Gly Tyr Xaa Ala Tyr Tyr Cys Glu Gly Glu Cys Xaa Phe
Pro
    20                  25                  30                  35

Leu Xaa Ser Xaa Met Asn Ala Thr Asn His Ala Ile Xaa Gln Xaa Leu Val His
Xaa
        40                  45                  50                  55

Xaa Xaa Pro Xaa Xaa Val Pro Lys Xaa Cys Cys Ala Pro Thr Xaa Leu Xaa Ala
            60                  65                  70

Xaa Ser VaI Leu Tyr Xaa Asp Xaa Ser Xaa Asn Val Ile Leu Xaa Lys Xaa Arg
75                  80                  85                  90

Asn Met Val Val Xaa Ala Cys Gly Cys His
        95                  100
```

wherein Xaa at res.2=(Lys or Arg); Xaa at res.3=(Lys or Arg); Xaa at res.11=(Arg or Gln); Xaa at res.16=(Gln or Leu); Xaa at res.19=(Ile or Val); Xaa at res.23=(Glu or Gln); Xaa at res.26=(Ala or Ser); Xaa at res.35=(Ala or Ser); Xaa at res.39=(Asn or Asp); Xaa at res.41=(Tyr or Cys); Xaa at res.50=(Val or Leu); Xaa at res.52=(Ser or Thr); Xaa at res.56=(Phe or Leu); Xaa at res.57=(Ile or Met); Xaa at res.58=(Asn or Lys); Xaa at res.60=(Glu, Asp or Asn); Xaa at res.61=(Thr, Ala or Val); Xaa at res.65=(Pro or Ala); Xaa at res.71=(Gln or Lys); Xaa at res.73=(Asn or Ser); Xaa at res.75=(Ile or Thr); Xaa at res.80=(Phe or Tyr); Xaa at res.82=(Asp or Ser); Xaa at res.84=(Ser or Asn); Xaa at res.89=(Lys or Arg); Xaa at res.91=(Tyr or His); and Xaa at res.97=(Arg or Lys).

In another embodiment, the morphogenic proteins comprise species of the generic amino acid sequence

```
1         10         20         30         40         50     (SEQ ID NO:10)
CXXXXLXVXFXDXGWXXWXXXPXGXXAXYCXGXCXXPXXXXXXXXNHAXX

          60         70         80         90         100
QXXVXXXXNXXXXPXXCCXPXXXXXXXXLXXXXXXXVXLXXYXXMXVXXCXCX
```

or residues 6–102 of SEQ ID NO:10, where the letters indicate the amino acid residues of standard single letter code, and the Xs represent any amino acid residues. Cysteine residues are highlighted.

Preferred amino acid sequences within the foregoing generic sequence (SEQ ID NO:10) are:

```
1        10        20        30        40        50    (SEQ ID NO:13)
LYVDFRDVGWNDWIVAPPGYHAFYCHGECPFPLADHLNSTNHAIVQTLVN
 K S S L  QE VIS E FD Y  E A AY MPESMKAS   VI SI H
 F E K I  DN     L    N  S   Q  ITK F P    TL    R
     A    S      K

         60        70        80        90        100
SVNPGKIPKACCVPTELSAISMLYLDENENVVLKNYQDMVVEGCGCR
AI SEQV EP    EQMNSLAI FFNDQDK I RK EE T DA H H
F    T   S     K DPV V  Y N S     H RN   RS
N    S                      K       P     E

and

1        10        20        30        40        50    (SEQ ID NO:14)
CKRHPLYVDFRDVGWNDWJVAPPGYHAFYCHGECPFPLADHLNSTNHAIV
 RRRS K S S L  QE VIS E FD Y  E A AY MPESMKAS   VI
   KE E E K I  DN     L    N  S   Q  ITK E P    TL
          A    S      K

        60        70        80        90        100
QTLVNSVNPGKIPKACCVPTELSAISMLYLDENENVVLKNYQDMVVEGCGCR
 SI HAI SEQV EP    EQMNSLAI FFNDQDK I RK EE T DA H H
    RF    T   S     K DPV V  Y N S     H RN   RS
     N    S                      K       P     E
```

wherein each of the amino acids arranged vertically at each position in the sequence may be used alternatively in various combinations (SEQ ID NO:10). These generic sequences have 6 or 7 cysteine residues where inter- or intra-molecular disulfide bonds can form. These sequences also contain other critical amino acids that influence the tertiary structure of the proteins.

In still another embodiment, useful morphogenic proteins comprise an amino acid sequence encoded by a nucleic acid that hybridizes, under low, medium or high stringency hybridization conditions, to DNA or RNA encoding reference morphogenic protein coding sequences., Exemplary reference sequences include the C-terminal sequences defining the conserved seven-cysteine domains of OP-1, OP-2, BMP-2, BMP-4, BMP-5, BMP-6, 60A, GDF-3, GDF-5, GDF-6, GDF-7, and the like. High stringent hybridization conditions are herein defined as hybridization in 40% formamtide, 5×SSPE, 5×Denhardt's Solution, and 0.1% SDS at 37° C. overnight, and washing in 0.1×SSPE, 0.1% SDS at 50° C. Standard stringency conditions are well characterized in commercially available, standard molecular cloning texts. See, for example, *Molecular Cloning, A Laboratory Manual*, 2nd Ed., ed. by Sambrook et al. (Cold Spring Harbor Laboratory Press 1989); *DNA Cloning*, Volumes I and II (D. N. Glover ed., 1985); *Oligonucleotide Synthesis* (M. J. Gait ed., 1984); *Nucleic Acid Hybridization* (B. D. Hames & S. J. Higgins eds. 1984), and B. Perbal, *A Practical Guide To Molecular Cloning* (1984).

Suitable in vitro, ex vivo and in vivo bioassays known in the art, including those described herein, may be used to ascertain whether a new BMP-related gene product has a morphogenic activity. Expression and localization studies defining where and when the gene is expressed may also be used to identify potential morphogenic activities. Nucleic acid and protein localization procedures are well known to those of skill in the art (see, e.g., Ausubel et al., eds. *Current Protocols in Molecular Cloning*, Greene Publishing and Wiley Interscience, New York, 1989).

Many of the identified BMPs are osteogenic and can induce bone and cartilage formation when implanted into mammals. Some BMPs identified based on sequence homology to known osteogenic proteins possess other morphogenic activities and a combination of a hormone and a soluble receptor thereof may be used to enhance those activities. For example, BMP-12 and BMP-13 reportedly induce ectopic formation of tendon/ligament-like tissue when implanted into mammals (Celeste et al., WO 95/16035). Using this bioassay, a skilled practitioner can readily identify one or more combinations of hormones and soluble receptors thereof that can stimulate the ability of the BMP to induce tendon/ligament-like tissue formation.

Certain BMPs which are known to be osteogenic can also induce neuronal cell differentiation. Embryonic mouse cells treated with BMP-2 or OP-1 differentiate into astrocyte-like (glial) cells, and peripheral nerve regeneration using BMP-2 has been reported (Wang et al., WO 95/05846). In addition, BMP-4, BMP-5 and OP-1 are expressed in epidermal ectoderm flanking the neural plate. Ectopic recombinant BMP-4 and OP-1 proteins can induce neural plate cells to initiate dorsal neural cell fate differentiation (Liem et al., *Cell*, 82, pp. 969–79 (1995)). At the spinal cord level, OP-1 and other BMPs can induce neural crest cell differentiation. It is suggested that OP-1 and these BMPs can induce many or all dorsal neural cell types, including roof plate cells, neural crest cells, and commissural neurons, depending on localized positional cues.

That several osteogenic proteins originally derived from bone matrix are involved in neural development suggests that these and other members of the BMP family have additional tissue inductive properties that are not yet disclosed. It is envisioned that the hormone/receptor combinations set forth in this invention can be used to enhance new or known tissue inductive properties of various known morphogenic proteins. It is also envisioned that the invention described herein will be useful for stimulating tissue inductive activities of new morphogenic proteins as they are identified in the future.

Production of Morphogenic Proteins

The morphogenic proteins of this invention can be derived from a variety of sources. For instance, they may be isolated from natural sources, recombinantly produced, or chemically synthesized.

A. Naturally Derived Morphogenic Proteins

The morphogenic proteins of the invention can be purified from tissue sources, e.g., mammalian tissue sources, using well known techniques. See, e.g., Oppermann et al., U.S. Pat. Nos. 5,324,819 and 5,354,557. If a purification protocol is unpublished, as for a newly identified morphogenic protein, conventional protein purification techniques (e.g., immunoaffinity) may be performed in combination with morphogenic activity assays. Such assays allow the trace of the morphogenic activity through a series of purification steps.

B. Recombinantly Expressed Morphogenic Proteins

In another embodiment of this invention, the morphogenic protein is produced by expressing an appropriate recombinant DNA molecule in a host cell. The DNA and amino acid sequences of many BMPs and OPs have been reported, and methods for their recombinant production are published and otherwise known to those of skill in the art. For a general discussion of cloning and recombinant DNA technology, see Ausubel et al., supra; see also Watson et al., *Recombinant* DNA, 2d ed. 1992 (W. H. Freeman and Co., New York).

The DNA sequences encoding bovine and human BMP-2 (formerly BMP-2A) and BMP-4 (formerly BMP-2B), and processes for recombinantly producing the corresponding proteins are described in U.S. Pat. Nos. 5,011,691, 5,013,649, 5,166,058 and 5,168,050. The DNA and amino acid sequences of human and bovine BMP-5 and BMP-6, and methods for their recombinant production, are disclosed in U.S. Pat. Nos. 5,106,748, and 5,187,076, respectively; see also U.S. Pat. Nos. 5,011,691 and 5,344,654. Methods for OP-1 recombinant expression are disclosed in Oppermann et al., U.S. Pat. Nos. 5,011,691 and 5,258,494. For an alignment of BMP-2, BMP-4, BMP-5, BMP-6 and OP-1 (BMP-7) amino acid sequences, see WO 95/16034. DNA sequences encoding BMP-8 are disclosed in WO 91/18098, and DNA sequences encoding BMP-9 in WO 93/00432. DNA and deduced amino acid sequences encoding BMP-10 and BMP-11 are disclosed in WO 94/26893, and WO 94/26892, respectively. DNA and deduced amino acid sequences for BMP-12 and BMP-13 are disclosed in WO 95/16035. The above patent disclosures, which describe DNA and amino acid sequences, and methods for producing the BMPs and OPs encoded by those sequences, are incorporated herein by reference.

To clone genes that encode new BMPs, OPs and other morphogenic proteins identified in extracts by bioassay, methods entailing "reverse genetics" may be employed. Such methods start with a protein of known or unknown function to obtain the gene that encodes that protein. Standard protein purification techniques may be used as an initial step. If enough protein can be purified to obtain a partial amino acid sequence, a degenerate DNA probe capable of hybridizing to the DNA sequence that encodes that partial amino acid sequence may be designed, synthesized and used as a probe to isolate full-length clones that encode that or a related morphogenic protein.

Alternatively, a partially-purified extract containing the morphogenic protein may be used to raise antibodies directed against that protein. Morphogenic protein-specific antibodies may then be used as a probe to screen expression libraries made from cDNAs (see, e.g., Broome and Gilbert, *Proc. Natl. Acad. Sci. U.S.A.*, 75, pp. 2746–49 (1978); Young and Davis, *Proc. Natl. Acad. Sci. U.S.A.*, 80, pp. 31–35 (1983)).

For cloning and expressing new BMPs, OPs and other morphogenic proteins identified based on DNA sequence homology, the homologous sequences may be cloned and sequenced using standard recombinant DNA techniques. With the DNA sequence available, a DNA fragment encoding the morphogenic protein may be inserted into an expression vector selected to work in conjunction with a desired host expression system. The DNA fragment is cloned into the vector such that its transcription is controlled by a heterologous promoter in the vector, preferably a promoter which may be optionally regulated.

Some host-vector systems appropriate for the recombinant expression of BMPs and OPs are disclosed in the references cited above. Useful host cells include but are not limited to bacteria such as *E. coli*, yeasts such as Saccharomyces and Picia, insects cells and other primary, transformed or immortalized eukaryotic cultured cells. Preferred eukaryotic host cells include CHO, COS and BSC cells (see below).

An appropriate vector is selected according to the host system selected. Useful vectors include but are not limited to plasmids, cosmids, bacteriophage, insect and animal viral vectors, including those derived from retroviruses and other single and double-stranded DNA viruses.

In one embodiment of this invention, the morphogenic protein may be derived from a recombinant DNA molecule expressed in a prokaryotic host. Using recombinant DNA techniques, various fusion genes have been constructed to induce recombinant expression of naturally sourced osteogenic sequences in *E. coli* (see, e.g., Oppermann et al., U.S. Pat. No. 5,354,557, incorporated herein by reference). Using analogous procedures, DNAs comprising truncated forms of naturally sourced morphogenic sequences may be prepared as fusion constructs linked by a sequence coding for the acid labile cleavage site (Asp-Pro) to a leader sequence (such as the "MLE leader") suitable for promoting expression in *E. coli.*

In another embodiment of this invention, the morphogenic protein is expressed using a mammalian host-vector system (e.g., transgenic production or tissue culture production). A morphogenic protein so expressed may resemble more closely the naturally occurring protein. While the glycosylation pattern of the recombinant protein may sometimes differ from that of the natural protein, such differences are often not essential for biological activity of the recombinant protein. Techniques for transfection, expression and purification of recombinant proteins are well known in the art. See, e.g., Ausubel et al., supra, and Bendig, *Genetic Engineering*, 7, pp. 91–127 (1988).

Mammalian DNA vectors should include appropriate sequences to promote expression of the gene of interest. Such sequences include transcription initiation, termination and enhancer sequences; efficient RNA processing signals such as splicing and polyadenylation signals; mRNA-stabilizing sequences; translation-enhancing sequences (e.g., Kozak consensus sequence); protein-stabilizing sequences; and when desired, sequences that enhance protein secretion.

Restriction maps and sources of various exemplary expression vectors designed for OP-1 expression in mammalian cells have been described in U.S. Pat. No. 5,354,557. Each of these vectors employs a full-length hOP-1 cDNA sequence inserted into the pUC-18 vector. It will be appreciated by those of skill in the art that DNA sequences encoding truncated forms of morphogenic proteins may also be used, provided that the expression vector or host cell provides the sequences necessary to direct processing and secretion of the expressed protein.

Useful promoters include, but are not limited to, the SV40 early and late promoters, the adenovirus major late promoter, the mouse metallothionein-1 ("mMT") promoter, the Rous sarcoma virus ("RSV") long terminal repeat ("LTR"), the mouse mammary tumor virus ("MMTV") LTR, and the human cytomegalovirus ("CMV") major intermediate-early promoter. For instance, a combination of the CMV or MMTV promoter with an enhancer sequence from the RSV LTR has been found to be particularly useful in expressing human osteogenic proteins.

Preferred DNA vectors also include a marker gene (e.g., neomycin or DHFR) and means for amplifying the copy number of the gene of interest. DNA vectors may also comprise stabilizing sequences (e.g., ori- or ARS-like sequences and telomere-like sequences), or may alternatively be designed to favor directed or non-directed integration into the host cell genome.

One method of gene amplification in mammalian cell systems is the use of the selectable dihydrofolate reductase (DHFR) gene in a dhfr cell line. Generally, the DHFR gene is provided on the vector carrying the gene of interest, and addition of increasing concentrations of the cytotoxic drug methotrexate (MTX) leads to amplification of the DHFR gene copy number, as well as that of the gene physically associated with it. DHFR as a selectable, amplifiable marker gene in transfected Chinese hamster ovary (CHO) cell lines is particularly well characterized in the art. Other useful amplifiable marker genes include the adenosine deaminase (ADA) and glutamine synthetase (GS) genes.

Gene amplification can be further enhanced by modifying marker gene expression regulatory sequences (e.g., enhancer, promoter, and transcription or translation initiation sequences) to reduce the levels of marker protein produced. Lowering the level of DHFR transcription increases the DHFR gene copy number (and the physically-associated gene) to enable the transfected cell to adapt to growth in even low levels of methotrexate (e.g., 0.1 $\mu$M MTX). Preferred expression vectors such as pH754 and pH752 (Oppermann et al., U.S. Pat. No. 5,354,557, FIGS. 19C and D) have been manipulated, using standard recombinant DNA technology, to create a weak DHFR promoter. As will be appreciated by those skilled in the art, other useful weak promoters, different from those disclosed herein, can be constructed using standard methods. Other regulatory sequences also can be modified to achieve the same effect.

Another gene amplification scheme relies on the temperature sensitivity (ts) of BSC40-tsA58 cells transfected with an SV40 vector. Temperature reduction to 33° C. stabilizes the temperature-sensitive SV40 T antigen, which leads to the excision and amplification of the integrated transfected vector DNA, thereby amplifying the physically-associated gene of interest.

The choice of cells/cell lines depends on the needs of the skilled practitioner. Monkey kidney cells (COS) provide high levels of transient gene expression and are thus useful for rapidly testing vector construction and the expression of cloned genes. COS cells expressing the gene of interest can be established by transfecting the cells with, e.g., an SV40 vector carrying the gene. Stably transfected cell lines, on the other hand, can be used for long term production of morphogenic proteins. By way of example, both CHO cells and BSC40-tsA58 cells can be used as host cells. Recombinant OP-1 has been expressed in three different cell expression systems: COS cells for rapidly screening the functionality of the various expression constructs, CHO cells for the establishment of stable cell lines, and BSC40-tsA58 cells as an alternative means of producing recombinant OP-1 protein.

Several bone-derived osteogenic proteins (OPs) and BMPs are found as homo- and heterodimers comprising interchain disulfide bonds in their active forms. For instance, BMP-2, BMP-4, BMP-6 and BMP-7 (OP-1)—originally isolated from bone—are bioactive as either homodimers or heterodimers. The ability of OPs and BMPs to form heterodimers may confer additional or altered morphogenic activities on morphogenic proteins. Heterodimers may exhibit qualitatively or quantitatively different binding affinities than homodimers for OP and BMP receptors. Altered binding affinities may in turn result in differential activation of receptors that mediate different signalling pathways, ultimately leading to different biological activities. Altered binding affinities can also be manifested in a tissue or cell type-specific manner, thereby inducing only particular progenitor cell types to undergo proliferation and/or differentiation.

The dimeric proteins can be isolated from the culture media and/or refolded and dimerized in vitro to form biologically active compositions. Heterodimers can be formed in vitro by combining separate, distinct polypeptide chains. Alternatively, heterodimers can be formed in a single cell by co-expressing nucleic acids encoding separate, distinct polypeptide chains. See, e.g., WO 93/09229 and U.S. Pat. No. 5,411,941, for exemplary protocols for heterodimer protein production.

C. In Vivo Expression of Morphogenic Proteins

The morphogenic protein of the invention can also be produced in vivo in a patient. To achieve this, an expression vector comprising a promoter operatively linked to a coding sequence of the morphogenic protein may be introduced into progenitor cells in the patient. Alternatively, one can isolate the appropriate progenitor cells from the patient, transfect or transduce the cells with the expression vector, and re-introduce the treated cells to the patient at a desired locus.

(1) Vectors

A nucleic acid construct according to this invention is derived from a non-replicating linear or circular DNA or RNA vector, or from an autonomously replicating plasmid or viral vector. Alternatively, the construct is integrated into the host genome. Any vector that can transfect or transduce the desired progenitor cell may be used. Preferred vectors are viral vectors, including those derived from replication-defective retroviruses (see, e.g., WO89/07136; Rosenberg et al., *N. Eng. J. Med.* 323(9): 570–578 (1990)), adenovirus (see, e.g., Morsey et al., *J. Cell. Biochem.*, Supp. 17E (1993)), adeno-associated virus (Kotin et al., *Proc. Natl. Acad. Sci. USA* 87:2211–2215 (1990)), replication-defective herpes simplex viruses (HSV; Lu et al., Abstract, page 66, Abstracts of the Meeting on Gene Therapy, Sept. 22–26, 1992, Cold Spring Harbor Laboratory, Cold Spring Harbor, N.Y.), vaccinia virus (Mukhedjee et al., *Cancer Gene Ther.* 7:663–70 (2000)), and any modified versions of these vectors. Methods for constructing expression vectors are well known in the art. See, e.g., Sambrook et al., *Molecular Cloning: A Laboratory Manual*, Cold Spring Harbor Laboratory, 2nd Edition, Cold Spring Harbor, N.Y., 1989).

(2) Expression Control Sequences

In these vectors, expression control sequences are operably linked to the nucleic acid sequence encoding the morphogenic protein useful in this invention. For eukaryotic cells, expression control sequences may include a promoter, an enhancer, such as one derived from an immunoglobulin gene, SV40, cytomegalovirus, etc., and a polyadenylation sequence. A nucleic acid construct of this invention may also contain an internal ribosome entry site ("IRES"), and an intron that may be desirably located between the promoter/ enhancer sequence and the morphogenic protein-coding sequence. Selection of these and other common vector elements are conventional. See, e.g., Sambrook et al, supra; Ausubel et al., *Current Protocols in Molecular Biology*, John Wiley & Sons, New York, (1989), and references cited therein.

In one embodiment of the present invention, high-level constitutive expression is desired. Exemplary promoters for this purpose include, without limitation, the retroviral Rous sarcoma virus (RSV) LTR promoter/enhancer, the cytomegalovirus (CMV) immediate early promoter/enhancer (see, e.g., Boshart et al, *Cell* 41:521–530 (1985)), the SV40 promoter, the dihydrofolate reductase promoter, the cytoplasmic β-actin promoter, the phosphoglycerol kinase (PGK) promoter. Useful promoters for BMP expression in osteoblasts also include the Type I collagen gene promoter and the CBFA gene promoter. Useful promoters for BMP expression in chondrocytes and chondroblasts include the Type II collagen gene promoter and the Type X collagen gene promoter. In another embodiment, the native transcription-regulatory elements of the desired morphogenic protein can be used.

Using the guidance provided by this application, one of skill in the art may make a selection among the above expression control sequences and modified versions thereof without departing from the scope of this invention.

(3) Administration of Nucleic Acid Constructs

The nucleic acid constructs of this invention may be formulated as a pharmaceutical composition for use in any form of transient and/or stable gene transfer in vivo and in vitro. The composition comprises at least the nucleic acid construct and a pharmaceutically acceptable carrier such as saline. Other aqueous and non-aqueous sterile suspensions known to be pharmaceutically acceptable carriers and well known to those of skill in the art may be employed also. The construct may be used for in vivo and ex vivo gene therapy, in vitro protein production and diagnostic assays.

The nucleic acid construct can be introduced into target cells as naked DNA, or by, e.g., liposome fusion (see, e.g., Nabel et al., *Science* 249:1285–8 (1990); Ledley, *J Pediatrics* 110:1–8 and 167–74 (1987); Nicolau et al., *Proc Natl Acad Sci USA* 80:1068–72 (1983)), erythrocyte ghosts, or microsphere methods (microparticles; see, e.g., U.S. Pat. No. 4,789,734; U.S. Pat. No. 4,925,673; U.S. Pat. No. 3,625,214; Gregoriadis, *Drug Carriers in Biology and Medicine*, pp. 287–341, Academic Press, 1979).

If the nucleic acid construct is viral-based, it can also be packaged as a virion which then is used to transduce a cell (e.g., an autologous T cell isolated from a patient) in vitro. The infected cell is then introduced into the patient. Alternatively, the recombinant virus may be administered to a patient directly, e.g., locally at the tissue defect site, or intravenously, intraperitoneally, intranasally, intramuscularly, subcutaneously, and/or intradermally, as determined by one skilled in the gene therapy art. A slow-release device, such as an implantable pump, may be used to facilitate delivery of the recombinant virus to a cell. Where the virus is administered to a subject, the specific cells to be infected may be targeted by controlling the method of delivery. The treatments of the invention may be repeated as needed, as determined by one skilled in the art.

Dosages of the nucleic acid construct of this invention in gene therapy will depend primarily on factors such as the condition being treated. The dosage may also vary depending upon the age, weight and health of the patient. For example, an effective human dosage of a BMP-coding virus is generally in the range of from about 0.5 ml to 50 ml of saline solution containing the virus at concentrations of about $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, or $1\times10^{16}$ viral particles per dose administered. The dosage will be adjusted to balance the corrective benefits against any adverse side effects. The levels of expression of BMP may be monitored to determine the type and frequency of dosage administration.

D. Synthetic Non-native Morphogenic Proteins

In another embodiment of this invention, a morphogenic protein may be prepared synthetically. Morphogenic proteins prepared synthetically may be native, or may be non-native proteins, i.e., those not otherwise found in nature.

Non-native morphogenic proteins can be made by mutating native morphogenic proteins. Methods for making mutations that favor refolding and/or assembling subunits into forms that exhibit greater morphogenic activity have been described. See, e.g., U.S. Pat. No. 5,399,677.

Non-native morphogenic proteins can also be synthesized using a series of consensus sequences (U.S. Pat. No. 5,324,819). These consensus sequences were designed based on partial amino acid sequence data obtained from native osteogenic products and on their homologies with other proteins reportedly having a presumed or demonstrated developmental function. Several biosynthetic consensus sequences (called consensus osteogernc proteins or "COPs") have been expressed as fusion proteins in prokaryotes. Purified fusion proteins may be cleaved, refolded, combined with a hormone and a soluble receptor thereof, implanted in an established animal model and examined for their bone- and/or cartilage-inducing activity. Certain preferred synthetic osteogenic proteins comprise one or both of two synthetic amino acid sequences designated COP5 (SEQ ID NO:11) and COP7 (SEQ ID NO:12).

The amino acid sequences of COP5 and COP7 are shown below, as set forth in Oppermann et al., U.S. Pat. Nos. 5,011,691 and 5,324,819, which are incorporated herein by reference:

COP5 LYVDFS-DVGWDDWIVAPPGYQAFYCHGEC PFPLAD

COP7 LYVDFS-DVGWNDWIVAPPGYHAFYCHGE CPFPLAD

COP5 HFNSTN-H-AVVQTLVNSVNSKI-PKACCVPT ELSA

COP7 HLNSTN-H-AVVQTLVNSVNSKI-PKACC VPTELSA

COP5 ISMLYLDENEKVVLKYNQEMVVEGCGCR (SEQ ID NO: 11)

COP7 ISMLYLDENEKVVLKYNQEMVVEGCGCR (SEQ ID NO: 12)

In these amino acid sequences, the dashes (-) are used as fillers only to line up comparable sequences in related proteins. Differences between the aligned amino acid sequences are highlighted.

In one embodiment of this invention, the morphogenic protein is a synthetic osteogenic protein comprising a partial or complete sequence of a generic sequence described above (SEQ ID NO:4, 5, 6, 7, or 10) such that it is capable of inducing tissue formation when properly folded and implanted in a mammal. For instance, the synthetic protein can induce bone formation from osteoblasts when implanted in a favorable environment; or it can promote cartilage formation when implanted in an avascular locus or when co-administered with an inhibitor of full bone development.

In another embodiment, the synthetic morphogenic protein of this invention comprises a sequence sufficiently duplicative of a partial or complete sequence of a COP, e.g., COP5 (SEQ ID NO:11) or COP7 (SEQ ID NO:12). Biosynthetic COP sequences are believed to dimerize during refolding and appear not to be active when reduced. Both homodimeric and heterodimeric COPs are contemplated in this invention. In certain embodiments, this synthetic protein is less than about 200 amino acids long.

These and other synthetic non-native osteogenic proteins may be used in concert with a hormone/receptor pair and tested using in vitro, ex vivo or in vivo bioassays for progenitor cell induction and tissue regeneration. The proteins in conjunction with the hormone/receptor pairs of this invention are envisioned to be useful for the repair and regeneration of bone, cartilage, tendon, ligament, neural and potentially other types of tissue.

Homologous Proteins Having Morphogenic Activity

The morphogenic proteins useful in this invention may be produced by recombinant expression of DNA sequences isolated based on homology with the osteogenic COP consensus sequences described above. Synthetic COP DNA sequences may be used as probes to retrieve related DNA sequences from a variety of species (see, e.g., Oppermann et al., U.S. Pat. Nos. 5,011,591 and 5,258,494, which are incorporated herein by reference).

Morphogenic proteins encoded by a gene that hybridizes with a COP sequence probe are assembled into two subunits disulfide-bonded to produce a heterodimer or homodimer capable of inducing tissue formation when implanted into a mammal. Recombinant BMP-2 and BMP-4 have been shown to have cross-species osteogenic activity as homodimers and as heterodimers assembled with OP-1 subunits. Morphogenic protein-encoding genes that hybridize to synthetic COP sequence probes include genes encoding Vg1, inhibin, DPP, OP-1, BMP-2 and BMP-4. Vg1 is a known *Xenoputs laevis* morphogenic protein involved in early embryonic patterning. Inhibin is another developmental gene that is a member of the BMP family of proteins from *Xenopus laevis*. DPP is an amino acid sequence encoded by a Drosophila gene responsible for development of the dorsoventral pattern. OP-1, BMP-2 and BMP-4 are osteogenic proteins that can induce cartilage, bone and neural tissue formation.

In another embodiment of this invention, a morphogenic protein may comprise a polypeptide encoded by a nucleic acid that hybridizes under stringent conditions to an "OPS" nucleic acid probe (Oppermann et al., U.S. Pat. No. 5,354, 557). "OPS"—standing for OP-1 "short"—refers to the portion of the human OP-1 protein defining the conserved 6 cysteine skeleton in the C-terminal active region (97 amino acids, SEQ ID NO:2, residues 335–431).

One example of a stringent hybridization condition is hybridization in 4×SSC at 65° C. (or 10° C. higher than the calculated melting temperature for a hybrid between the probe and a nucleic acid sequence containing no mismatched base pairs), followed by washing in 0.1×SSC at the hybridization temperature. Another stringent hybridization condition is hybridization in 50% formamide, 4×SSC at 42° C.

Thus, in view of this disclosure, the skilled practitioner can readily design and synthesize genes, or isolate genes from cDNA or genomic libraries that encode amino acid sequences having morphogenic activity. These genes can be expressed in prokaryotic or eukaryotic host cells to produce large quantities of active osteogenic or otherwise morphogenic proteins. The recombinant proteins may be in native, truncated, mutant, fusion, or other active forms capable of inducing formation of bone, cartilage, or other types of tissue, as demonstrated by in vitro and ex vivo bioassays and in vivo implantation in mammals, including humans.

Hormones and Receptors Thereof

A hormone/receptor pair of this invention is capable of stimulating the ability of a morphogenic protein to induce tissue formation from a progenitor cell. In a method of this invention, the tissue inductive activity of a morphogenic protein in a mammal is improved by co-administering effective amounts of a hormone and a soluble receptor thereof. Alternatively, the morphogenic protein and the hormone/receptor pair are administered sequentially. It has been found that the synergism between a morphogenic protein and a hormone/receptor pair is preserved even if the morphogenic protein is administered 4 to 8 hours before the hormone/receptor pair. The morphogenic protein, the hormone, and the hormone receptor can also be administered separately.

One or more hormone/receptor pairs can be selected for use in concert with one or more morphogenic proteins according to the desired tissue type to be induced and the site at which the treatment will be administered. The particular choice of a morphogenic protein(s)/hormone(s)/receptor(s) combination and the relative concentrations at which they are combined may be varied systematically to optimize the tissue type induced at a selected treatment site using the procedures described herein.

Hormones useful in this invention include, but are not limited to, interleukins 1 through 18, fibroblast growth factor, vascular endothelial growth factor, platelet-derived growth factor, TGF-β, and prostaglandins (e.g., E1 and E2). It may be preferred that the target cell has a cell-surface receptor for the hormone. The hormones can also be morphogenic proteins such as GDFs; as a result, the composition of this invention will contain two morphogenic proteins and a soluble receptor of one of these proteins.

One preferred hormone/receptor pair of this invention is IL-6/sIL-6R. IL-6 is a member of a subfamily of multifunctional hormones. It appears to play a role in both bone formation and bone resorption by affecting mitogenesis of target cells and regulating the synthesis of other local factors. Clinical studies show that IL-6 is involved in a variety of diseases, such as fibrous dysplasia, osteopenia, osteoporosis and Paget's disease. Recombinant fall length human IL-6 (26 ID) expressed from *E: coli* can be obtained from Sigma (St. Louis, Mich.) and Promega (Madison, Wis.). Recombinant sIL-6R produced from baculovirus and containing the entire extracellular domain (residues 1–339; 38 kD) of human IL-6R can be obtained from Sigma and R&D Systems (Minneapolis, Minn.). See also Examples 1 and 2, infra. Active allelic, species or other variants of these IL-6 and sIL-6 products can also be used.

The hormone or the hormone receptor of this invention can be associated with an agent that is capable of increasing the hormone's or receptor's bio-activity, e.g., synthesis, half-life, bio-availability, and reactivity with other biomolecules such as binding proteins and receptors. These agents may contain carrier molecules such as proteins and lipids.

The hormone and hormone receptor are present in amounts capable of synergistically stimulating the tissue inductive activity of the morphogenic protein in a mammal. The relative concentrations of morphogenic protein, hormone and hormone receptor that optimally induce tissue formation may be determined empirically by the skilled practitioner using the procedures described herein.

Progenitor Cells

The progenitor cell that is induced to proliferate and/or differentiate by the morphogenic protein of this invention is preferably a mammalian cell. Examples of useful progenitor cells are mammalian chondroblasts, osteoblasts and neuroblasts, all earlier developmental precursors thereof, and all cells that develop therefrom (e.g., pre-chondroblasts and chondrocytes). The progenitor cell may be induced to form one or more tissue types such as endochondral or intramembranous bone, cartilage, tendon/ligament-like tissue, neural tissue and kidney tissue. The specific morphogenic activity exhibited by a morphogenic protein will depend in part on the type of the progenitor cell as well as the treatment site. These variables may be tested empirically.

Morphogehic proteins are highly conserved throughout evolution, and non-mammalian progenitor cells are likely to be stimulated by same- or cross-species morphogenic proteins and hormone/receptor combinations. It is thus envisioned that where schemes are available for implanting xenogeneic cells into humans without adverse immunological reactions, non-mammalian progenitor cells stimulated by morphogenic protein and a hormone/receptor pair according to the procedures set forth herein will be useful for tissue regeneration and repair in humans.

Testing Morphogenic Activity

To identify a hormone/receptor pair capable of stimulating the tissue inductive activity of a chosen morphogenic protein, an appropriate assay is selected. Initially, in vitro assays can be performed. A useful in vitro assay may monitor a nucleic acid or protein marker whose expression is known to correlate with the associated cell differentiation pathway. See, e.g., Examples 3 and 4 of U.S. Pat. No. 5,854,207, Lee et al.; and Examples 1 and 2, infra.

Examples 1 and 2, infra, describe experiments using OP-1 to identify and to optimize an effective concentration of IL-6 and sIL-6R. OP-1 is known to have osteogenic and neurogenic activity. Thus, to identify a hormone/receptor pair having synergistic effects with OP-1, one can conduct an in vitro assay that examines the expression of a molecular marker, e.g., an osteogenic- or a neurogenic-associated marker, in appropriate progenitor cells.

One useful assay for testing potential hormone/receptor pairs with OP-1 for osteogenic activity is the alkaline phosphatase ("AP") enzymatic assay. AP is an osteoblast differentiation marker in primary osteoblastic fetal rat calvarial ("FRC") cells. The OP-1-stimulated AP activity results from increased steady-state AP mRNA levels. Other useful protein markers for monitoring osteogenic activity of a composition include, but are not limited to, type I collagen, osteocalcin, osteopontin, bone sialoprotein and PTH-dependent cAMP levels.

An AP assay is performed generally as follows. First, a hormone/receptor pair is identified by picking various concentrations and ratios of the hormone and hormone receptor and testing them in the absence and presence of a morphogenic protein. Second, the amounts of hormone and hormone receptor required to achieve optimal, preferably synergistic, tissue induction in concert with the morphogenic protein is determined by generating dose response curves.

Optionally, additional hormone/receptor pairs that further stimulate or otherwise alter the morphogenic activity induced by a morphogenic protein and a first hormone/receptor pair may be identified and a new multi-factor dose response curve generated. See, e.g., Example 5 of U.S. Pat. No. 5,854,207.

Bone Induction Assays

The various morphogenic compositions and devices of this invention can also be evaluated with ex vivo or in vivo bioassays. A rat bioassay for bone induction may be used to monitor osteogenic activity of osteogenic proteins in concert with one or more hormone/receptor pairs. See, e.g., Sampath et al., *Proc. Natl. Acad. Sci. USA*, 80, pp. 6591–95 (1983), and U.S. Pat. No. 5,854,207, Example 7. Rat bioassays are useful as the first step in moving from in vitro studies to in vivo studies.

Large animal efficacy models for osteogenic device testing are known in the art. Exemplary models are the feline femoral model, the rabbit ulnar model, the dog ulnar model and the monkey model. See, e.g., U.S. Pat. Nos. 5,354,557, and 5,854,207 (Examples 10 and 11 therein).

In general, about 500–1000 ng of active morphogenic protein and about 10–200 ng of active hormone and active hormone receptor are combined with 25 mg of a carrier matrix for rat bioassays. In larger animals, typically about 0.8–1 mg of active morphogenic protein per gram of carrier is combined with about 100 ng or more of an active hormone and hormone receptor. The optimal ratios of morphogenic protein to hormone and of hormone to hormone receptor for a specific tissue type may be determined empirically by those of skill in the art according to the procedures set forth herein. Greater amounts may be used for large implants.

Tendon/ligament-like Tissue Formation Bioassay

Assays for monitoring tendon and ligament-like tissue formation induced by morphogenic proteins are known in the art. See, e.g., Celeste et al., WO 95/16035, hereby incorporated by reference. Such assays can be used to identify hormone/receptor pairs that stimulate tendon/ligament-like tissue formation by BMP-12, BMP-13 or other morphogenic proteins in a particular treatment site. The assays may also be used to optimize concentrations and treatment schedules for therapeutic tissue repair regiments.

These assays may be used to test various combinations of morphogenic protein and hormone/receptor combinations, and to produce an in vivo dose response curve for determining the effective relative concentrations of morphogenic proteins and hormones/receptors.

Neural Assays

The osteogenic proteins BMP-4 and BMP-7 (OP-1) can induce ventral neural plate explants to undergo differentiation into dorsal neural cell fates (Liem et al., *Cell*, 82, pp. 969–79 (1995)). Molecular markers of dorsal cell differentiation are described in Liem et al. These markers include PAX3 and MSX, whose expression delineates an early stage of neural plate cell differentiation; DSL-1, a BMP-like molecule delineating differentiation of dorsal neural plate cells at a stage after neural tube closure; and SLUG protein, whose expression after neural tube closure defines premigratory neural crest cells. Expression of these dorsal markers can be induced in ventral neural plate explants by ectopic BMP4 and OP-1.

A peripheral nerve regeneration assay using BMP-2 has been described (Wang et al., WO 95/05846, hereby incorporated by reference). The assay involves the implantation of neurogenic devices in the vicinity of severed sciatic nerves in rats. This procedure may be used to assess the ability of a putative hormone/receptor pair to enhance the neuronal inductive activity of homo- and heterodimers of morphogenic proteins having neurogenic activity, such as BMP-2, BMP-4, BMP-6 and OP-1, or of any selected neurogenic protein/hormone/hormone receptor combinations.

Pharmaceutical Compositions

The pharmaceutical compositions of this invention contain at least one (e.g., at least 2, 3 or 5) morphogenic protein, and at least one (e.g., at least 2 or 3) hormone/receptor pair. These compositions are capable of inducing tissue formation when administered, e.g., implanted, into a patient. The compositions will be administered at an effective dose to induce the particular type of tissue at the desired treatment site. Determination of a preferred pharmaceutical formulation and a therapeutically efficient dose regiment for a given application is well within the skill of the art. Factors that need to be considered include, for example, the administration mode, the condition and weight of the patient, the extent of desired treatment and the tolerance of the patient for the treatment.

Doses expected to be suitable starting points for optimizing treatment regiments are based on the results of in vitro assays, and ex vivo or in vivo assays. Based on the results of such assays, a range of suitable morphogenic protein and hormone/receptor concentration ratios can be selected to test at a treatment site in animals and then in humans.

The pharmaceutical compositions of this invention may be in a variety of forms. These include, for example, solid, semi-solid and liquid forms such as tablets, pills, powders, liquids, suspensions, suppositories, gels, pastes, and other injectable and infusible solutions. The preferred form depends on the intended mode of administration and therapeutic application. Modes of administration may include oral, parenteral, subcutaneous, intravenous, intralesional or topical administration. In most cases, the pharmaceutical compositions of this invention will be administered in the vicinity of or at the treatment site in need of tissue regeneration or repair.

The pharmaceutical compositions of this invention may, for example, be placed into sterile, isotonic formulations with or without co-factors which stimulate uptake or stability. For example, the compositions may contain a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions may also include pharmaceutically acceptable carriers well known in the art. See, for example, Remington's Pharmaceutical Sciences, 16th Edition, 1980, Mac Publishing Company. Such pharmaceutically acceptable carriers may include other medicinal agents, carriers, genetic carriers, adjuvants, and excipients such as human serum albumin or plasma preparations. The compositions may be in the form of a unit dose and will usually be administered as a dose regiment that depends on the particular tissue treatment.

The pharmaceutical compositions of this invention may also be administered in form of a morphogenic device using, for example, microspheres, liposomes, other microparticulate delivery systems or sustained release formulations placed in, near, or otherwise in communication with affected tissues or the bloodstream bathing those tissues.

Liposomes containing the polypeptide mixtures of this invention can be prepared by well-known methods. See, e.g. DE 3,218,121; Epstein et al., *Proc. Natl. Acad. Sci. U.S.A.*, 82, pp. 3688–92 (1985); Hwang et al., *Proc. Natl. Acad. Sci. U.S.A.*, 77, pp. 4030–34 (1980); U.S. Pat. Nos. 4,485,045 and 4,544,545. Ordinarily the liposomes are of the small (about 200–800 Angstroms) unilamellar type in which the lipid content is greater than about 30 mol. % cholesterol. The proportion of cholesterol is selected to control the optimal release rate of the polypeptides of interest.

The polypeptide mixtures of this invention may also be attached to liposomes containing other biologically active molecules to modulate the rate and characteristics of tissue induction. Such attachment may be accomplished by cross-linking agents such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide. See, e.g., Duzgunes et al., *J. Cell. Biochem. Abst.*, Suppl. 16E 77 (1992).

Morphogenic Devices

The pharmaceutical compositions of this invention can additionally contain an implantable, biocompatible carrier. Such compositions are also called morphogenic devices. The carrier functions as a sustained release delivery system for the therapeutic proteins and protects the proteins from non-specific proteolysis. The carrier may be biodegradable in vivo. A sustained release carrier may contain semipermeable polymer matrices in the form of shaped articles, e.g., suppositories or capsules. Such a carrier can be made of polylactides (U.S. Pat. No. 3,773,319; EP 58,481), copolymers of L-glutamic acid and ethyl-L-glutamate (Sidman et al., *Biopolymers*, 22, pp. 547–56 (1985)); poly(2-hydroxyethyl-methacrylate) or ethylene vinyl acetate (Langer et al., *J. Biomed. Mater. Res.*, 15, pp. 167–277 (1981); Langer, *Chem. Tech.*, 12, pp. 98–105 (1982)).

The carrier may also serve as a temporary scaffold and substratum for recruitment of migratory progenitor cells and their subsequent anchoring and proliferation, until replaced by new bone or other appropriate tissue. For example, the carrier may contain a biocompatible matrix made up of particles or otherwise having the desired porosity or microtexture. The pores will permit migration, anchoring, differentiation and proliferation of the relevant progenitor cells. The particle size may be within the range of 70 $\mu$m–850 $\mu$m, e.g., 70 $\mu$m–420 $\mu$m or 150 $\mu$m–420 $\mu$m. A particulate matrix may be fabricated by close packing particulate materials into a shape spanning the tissue defect to be treated. Various matrices known in the art can be employed. See, e.g., U.S. Pat. Nos. 4,975,526, 5,162,114 and 5,171,574, and WO 91/18558, all of which are herein incorporated by reference.

Useful matrix materials include but are not limited to collagen; celluloses, including carboxymethyl cellulose; homo- or co-polymers of glycolic acid, lactic acid, and butyric acid, including derivatives thereof, and ceramics, such as hydroxyapatite, tricalcium phosphate and other calcium phosphates. See, e.g., U.S. Pat. No. 5,854,207, col. 25, line 59, through col. 27, line 6. Various combinations of these or other suitable matrix materials may be useful as determined by the assays set forth herein. The choice of material depends in part on its in vivo dissolution rate. In bones, the dissolution rates can vary according to whether the implant is placed in cortical or trabecular bone.

Other useful matrices include particulate, demineralized, guanidine-extracted, allogenic bone; and specially treated, particulate, protein-extracted, demineralized xenogenic bone. See, e.g., Example 6 of U.S. Pat. No. 5,854,207. Such xenogenic bone powder matrices may be treated with proteases such as trypsin. Preferably, the xenogenic matrices are treated with one or more fibril-modifying agents to increase the intraparticle intrusion volume (porosity) and surface area. Useful modifying agents include solvents such as dichloromethane, trichloroacetic acid, acetonitrile and acids such as trifluoroacetic acid and hydrogen fluoride. A preferred fibril-modifying agent is in the form of a heated aqueous medium, preferably an acidic aqueous medium having a pH less than about 4.5, most preferably having a pH between about 2 and 4, inclusive. The acidic aqueous medium can, for instance, be 0.1% acetic acid with a pH of about 3. Heating demineralized, delipidated, guanidine-extracted bone collagen in an aqueous medium at elevated temperatures (e.g., at about 37° C.–65° C., preferably at about 45° C.–60° C.) for approximately one hour is generally sufficient to achieve the desired surface morphology. It is hypothesized that the heat treatment alters the collagen fibrils, resulting in an increase in the particle surface area.

Xenogenic bone matrices can be used in a variety of clinical settings. In addition to its use as a matrix for bone formation in various orthopedic, periodontal, and reconstructive procedures, the matrix also may be used as a sustained release carrier, or as a collagenous coating for orthopedic or general prosthetic implants.

Demineralized guanidine-extracted xenogenic bovine bone contains a mixture of additional materials that may be fractionated further using standard biomolecular purification techniques. For example, bone extracts can be fractionated by chromatography, and the various extract fractions corresponding to the chromatogram peaks can be added back together to an active matrix. Doing so may remove inhibitors of bone or tissue-inductive activity, thereby improving matrix properties.

Besides morphogenic proteins and hormone/receptor pairs, the morphogenic devices of this invention may additionally contain other hormones and trophic agents. The devices may also contain antibiotics, chemotherapeutic agents, enzymes, enzyme inhibitors and other bioactive agents. These ingredients may be adsorbed onto or dispersed within the carrier, and will be released over time at the implantation site as the carrier material is slowly absorbed.

General Consideration of Matrix Properties

Factors influencing the performance of a matrix include matrix geometry, particle size (if the matrix is made up of particles), the methodology for combining the matrix and morphogenic proteins, the degree of both intra- and inter-particle porosity, the presence of mineral, and the presence of surface charge. For example, studies have shown that, in bone induction using OP-1 and a morphogenic protein stimulating factor, perturbation of the matrix charge by chemical modifications can abolish bone inductive responses. Particle size also influences the quantitative response of new bone, with sizes between 70 $\mu$m and 420 $\mu$m capable of eliciting the maximum response. Further, contamination of the matrix with bone mineral may inhibit bone formation. Individual heavy metal concentrations in a bone matrix can be reduced to less than about 1 ppm by the methods described herein.

The sequential cellular reactions at the interface of the bone matrix and an osteogenic protein implant are complex. The multi-step cascade includes: binding of fibrin and fibronectin to the implanted matrix, migration and proliferation of mesenchymal cells, differentiation of the progenitor cells into chondroblasts, cartilage formation, cartilage calcification, vascular invasion, bone formation, remodeling, and bone marrow differentiation. A successful matrix is capable of accommodating each of these steps.

The matrix may be shaped as desired in anticipation of surgery or shaped by the physician or technician during surgery. It has been shown that new bone is formed essentially with the dimensions of the implanted device. In the case where the matrix material is biodegradable in vivo, the matrix material is slowly absorbed by the body and is replaced by new bone in the shape of; or very nearly the shape of, the implant. Thus, the matrix is preferably shaped to span a tissue defect and to take the desired form of the new tissue. For example, in the case of bone repair of a non-union defect, it is desirable to use dimensions that span the non-union, and the new bone will eventually fill the defect.

The matrix may be a shape-retaining solid made of loosely-adhered particulate material, e.g., collagen. Alternatively, the matrix may be a molded, porous solid, or an aggregation of close-packed particles held in place by surrounding tissue. Masticated muscle or other tissue may also be used. Large allogenic bone implants can act as a carrier for the matrix if their marrow cavities are cleaned and packed with particles containing dispersed osteogenic protein and hormone/receptor pair.

The matrix may also take the form of a paste or a hydrogel. “Hydrogel” refers to a three dimensional network of cross-linked hydrophilic polymers in the form of a gel. The gel is substantially composed of water, for instance, greater than 90% water. Hydrogel matrices can carry a net positive or net negative charge, or may be neutral. A typical net negative charged matrix is alginate. Hydrogels carrying a net positive charge are, for example, extracellular matrix components such as collagen and laminin. Examples of commercially available extracellular matrix components include MATRIGEL™ and VITROGEN™. Example of a net neutral hydrogel are highly cross-linked polyethylene oxide and polyvinyl alcohol.

Prosthetic Devices

This invention also features an implantable prosthetic device comprising at least one morphogenic protein and at least one hormone/receptor pair at therapeutic amounts and ratios. The device can be used in conjunction with a composition containing the same or other morphogenic protein or hormone/receptor pair. The prosthetic device may be made from a material containing metal or ceramic. Exemplary prosthetic devices are hip devices, screws, rods and titanium cages for spine fusion. The device is implanted in a mammal (e.g., a human) at a locus where the target tissue and the surface of the prosthetic device are maintained at least partially in contact for a time sufficient to permit enhanced tissue growth between the target tissue and the device.

The osteogenic composition may be disposed on the prosthetic implant on a surface region that is to be positioned next to a target tissue in the mammal. Preferably, the mammal is a human patient. The composition is disposed in an amount sufficient to promote enhanced tissue growth into the implant or onto its surface. The amount of the composition to be used may be determined empirically by using bioassays such as those described herein and in Rueger et al., U.S. Pat. No. 5,344,654, which is incorporated herein by reference. Preferably, animal studies are performed to optimize the concentration of the ingredients in the device before a similar prosthetic device is used in a human patient. The prosthetic devices will be useful for repairing orthopedic defects, injuries or anomalies in the treated mammal.

Utility of Morphogenic Compositions and Devices

The compositions, devices and methods of this invention will permit a physician to treat a variety of tissue injuries, tissue degenerations, and other diseased tissue conditions. The compositions and devices can ameliorate or remedy these conditions by stimulating local tissue formation or regeneration.

The devices of this invention may be implanted at the desired locus in a mammal such that the implant is accessible to the appropriate progenitor cells of this mammal. The devices may be used alone or in combination with other therapies for tissue repair and regeneration.

The morphogenic devices of this invention may also be implanted in or surrounding a joint for use in cartilage and soft tissue repair, or in or surrounding nervous system-associated tissue for use in neural regeneration and repair. The tissue specificity of the particular morphogenic protein—or combination of morphogenic proteins with other biological factors—will determine the cell types or tissues that will be amenable to such treatments and can be selected by one skilled in the art. The ability to enhance morphogenic protein-induced tissue regeneration by co-administering a hormone/receptor pair according to the present invention is thus not believed to be limited to any particular cell-type or tissue.

The osteogenic compositions and devices of this invention will permit the physician to obtain predictable bone, ligament and/or cartilage formation using less osteogenic protein to achieve at least about the same extent of bone or cartilage formation.

The osteogenic compositions and devices of this invention may be used to treat more effectively the injuries, anomalies and disorders that have been described in the prior art of osteogenic devices. These include, for example, forming local bone in fractures, non-union fractures, fusions and bony voids such as those created in tumor resections or those resulting from cysts; treating acquired and congenital craniofacial and other skeletal or dental anomalies (see e.g., Glowacki et al., *Lancet*, 1, pp. 959–63 (1981)); performing dental and periodontal reconstructions where lost bone replacement or bone augmentation is required such as in a jaw bone; and supplementing alveolar bone loss resulting from periodontal disease to delay or prevent tooth loss (see e.g., Sigurdsson et al., *J. Periodontol.*, 66, pp. 511–21 (1995)).

An osteogenic device of this invention that comprises a matrix comprising allogenic bone may also be implanted at a site in need of bone replacement to accelerate allograft repair and incorporation in a mammal. Another potential clinical application of the improved osteogenic devices of this invention is in cartilage repair, for example, following joint injury or in the treatment of osteoarthritis. The ability to enhance the cartilage-inducing activity of morphogenic proteins by co-administering a hormone/receptor pair may permit faster or more extensive tissue repair and replacement using the same or lower levels of morphogenic proteins.

The morphogenic compositions and devices of this invention will be useful in treating certain congenital diseases and developmental abnormalities of cartilage, bone and other tissues. For example, homozygous OP-1-deficient mice die within 24 hours after birth due to kidney failure (Luo et al., *J. Bone Min. Res.*, 10 (Supp. 1), pp. S163 (1995)). Kidney failure in these mice is associated with the failure to form renal glomeruli due to lack of mesenchymal tissue condensation. OP-1-deficient mice also have various skeletal abnormalities associated with their hindlimbs, rib cage and skull, are polydactyl, and exhibit aberrant retinal development. These results, in combination with those discussed above concerning the ability of OP-1 to induce differentiation into dorsal neural cell fates, indicate that OP-1 plays an important role in epithelial-mesenchymal interactions during development. It is anticipated that the compositions, devices and methods of this invention will be useful for ameliorating these and other developmental abnormalities.

Developmental abnormalities of the bone may affect isolated or multiple regions of the skeleton or of a particular supportive or connective tissue type. These abnormalities often require complicated bone transplantation procedures and orthopedic devices. The tissue repair and regeneration required after such procedures may occur more quickly and completely with the use of morphogenic compositions, devices and methods of this invention.

Examples of heritable conditions, including congenital bone diseases, for which use of the morphogenic compositions and devices of this invention will be useful include osteogenesis imperfecta, the Hurler and Marfan syndromes, and several disorders of epiphyseal and metaphyseal growth centers such as is presented in hypophosphatasia, a deficiency in alkaline phosphatase enzymatic activity.

Inflammatory joint diseases may also benefit from the improved methods, compositions and devices of this invention. These diseases include but are not limited to rheumatoid and psoriatic arthritis, bursitis, ulcerative colitis, regional enteritis, Whipple's disease, ankylosing spondylitis (also called Marie Strümpell or Bechterew's disease), and the so-called "collagen diseases" such as systemic lupus erythematosus (SLE), progressive systemic sclerosis (scleroderma), polymyositis (dermatomyositis), necrotizing vasculitides, Sjögren's syndrome (sicca syndrome), rheumatic fever, amyloidosis, thrombotic thrombocytopenic purpura and relapsing polychondritis. Heritable disorders of connective tissue include Marfan's syndrome, homocystinuria, Ehlers-Danlos syndrome, osteogenesis imperfecta, alkaptonuria, pseudoxanthoma elasticum, cutis laxa, Hurler's syndrome, and myositis ossificans progressiva.

EXAMPLES

The following are examples which illustrate the morphogenic compositions and devices of this invention, and methods used to characterize them. These examples should not be construed as limiting. They are included for purposes of illustration and the present invention is limited only by the claims.

Example 1

FIG. 1 shows the effects of Il-6, sIL-6R, and mixtures of recombinant human IL-6 and recombinant human sIL-6R ("IL-6/R"), respectively, on the OP-1-induced AP activity in FRC cells. Confluent FRC cells were treated with the indicated agent(s) for 24 hrs. The concentrations of agent(s) used (ng/ml) are indicated in parentheses. For IL-6/R, the molar ratio of the two was maintained at about 1.2, and their respective amounts are indicated also in parentheses. Total AP activity was determined spectrophotometrically. Total cellular protein was determined by the Bradford Assay.

Specific AP activity was calculated as AP/protein unit. AP activity values were normalized to that of 150 ng/ml OP-1 (=1) and represent the means of 8–12 independent determinations using 3 different FRC cell preparations.

As shown in FIG. 1, IL-6 alone in the concentration range tested did not stimulate the basal AP activity. SIL-6R alone stimulated the basal AP activity slightly; however, the stimulation did not seem to be sIL-6R dose-dependent.

FIG. 1 further demonstrates that IL-6 potentiates the OP-1-induced AP activity in a dose-dependent manner. A maximum of about 2-fold stimulation was observed ($p<0.05$). SIL-6R also potentiated the OP-1-induced AP activity in a dose-dependent manner. A higher fold (about 3.5-fold; $p<0.02$) of stimulation than observed with IL-6 was achieved.

The effect of IL-6/R on the OP-1-induced AP activity was also examined. At the highest tested dose of IL-6 plus its soluble receptor (100 ng/ml IL-6 and 125 ng/ml sIL-6R), the OP-1-induced AP activity was synergistically enhanced by about 10-fold. This enhancement was reproducible. However, at the lower dose range, the IL-6/R combination did not appear to stimulate beyond what was achieved by either IL-6 or its receptor alone; on the contrary, the combination appeared to suppress AP activity.

Example 2

Figure 2:
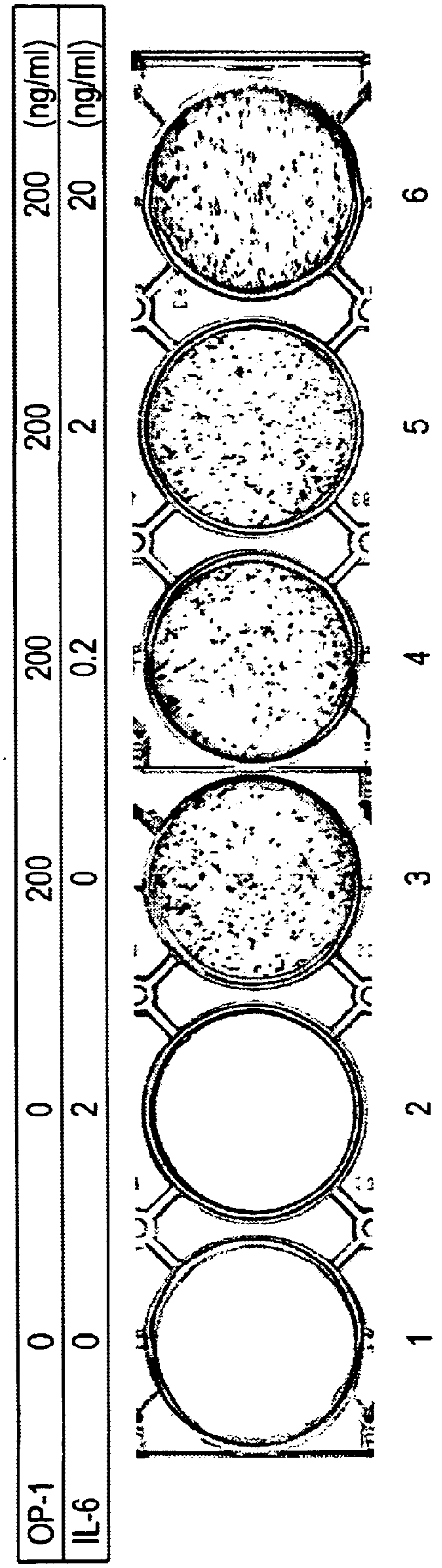
FIG. 2 is a photograph showing results of a mineralized bone nodule formation assay using OP-1 and IL-6. Dark spots inside the wells represent mineralized bone nodules.
Figure 3:
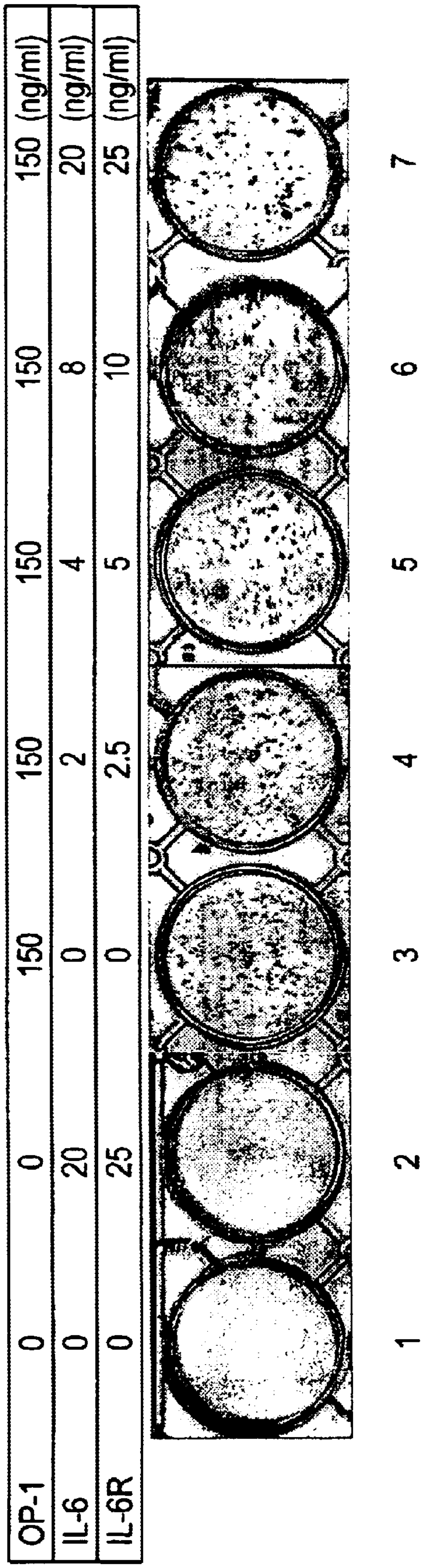
FIG. 3 is a photograph showing results of a mineralized bone nodule formation assay using OP-1, IL-6 and sIL-6R. Dark spots inside the wells represent mineralized bone nodules.

FIG. 2 shows that IL-6 alone enhanced OP-1 action in a mineralized bone nodule formation assay. FRC cells were grown in αMEN (supplemented with 5% FBS, 30 μg/ml gentamycin, 100 μg/ml ascorbic acid and 5 mM β-glycerolphosphate), and treated for various durations of time with (1) solvent vehicle, (2) 200 ng/ml OP-1, or (3) 200 ng/ml OP-1 plus IL-6 at various concentrations. The culture media were replenished with the same treatment agent(s) every three days. Progress of nodule formation was monitored every three days. After a total of 15 days, cells were fixed with formalin and photographed. As seen in FIG. 3, IL-6/R also enhanced OP-1's ability to induce the formation of mineralized bone nodules.

Example 3

To determine whether IL-6/R effects its synergy with OP-1 by directly stimulating OP-1 responsive cells or by increasing the number of OP-1 responsive cells, primary cultures of FRC were used as a model system, in which AP activity levels were used as a biochemical marker of OP-1 responsiveness. Histochemical data showed that the number of AP positive cells in cultures treated with IL-6/R (40 ng/ml IL-6 and 50 ng/ml sIL-6R) and OP-1 (200 ng/ml) was similar to that in cultures treated with OP-1 alone (200 ng/ml). However, the AP activity level was higher in the former cultures than the latter cultures. IL-6 alone (40 ng/ml) did not stimulate AP positive cells; and sIL-6R alone (50 ng/ml) or IL-6/R (40 ng/ml IL-6 and 50 ng/ml sIL-6R) stimulated AP positive cells to a smaller extent, as compared to the combination of IL-6/R and OP-1. These data suggest that IL-6/R's synergistic effect on OP-1 results from IL-6/R's direct stimulation of OP-1 responsive cells.

Example 4

To investigate whether IL-6/R stimulates the expression of OP-1 receptors on FRC cells, the mRNA levels of three BMP type I receptors (BMPR-IA, BMPR-IB, and ActR-I) and one BMP type II receptor (BMPR-II) were measured by Northern blot analysis.

Briefly, confluent FRC cells were treated for 48 hours with (1) a vehicle; (2) 200 ng/ml OP-1; (3) 40 ng/ml IL-6 and 50 ng/ml sIL-6R; or (4) 200 ng/ml OP-1, 40 ng/ml IL-6, and 50 ng/ml sIL-6R. Total RNA was isolated using the TRI reagent (Sigma) and loaded onto an AGAROSE GTG (FMC) gel containing formaldehyde. Northern blots were prepared and probed with $^{32}P$-labeled cDNA encoding for the various BMPRs. These probes hybridized only to mRNA. The radioactive bands were detected and quantified using a PHOSPHORIMAGER (Molecular Dynamics, Sunnyvale, Calif.). To normalize the band intensity of the BMPR bands, the blots were also probed with an oligonucleotide for the 18S rRNA.

Figure 4:
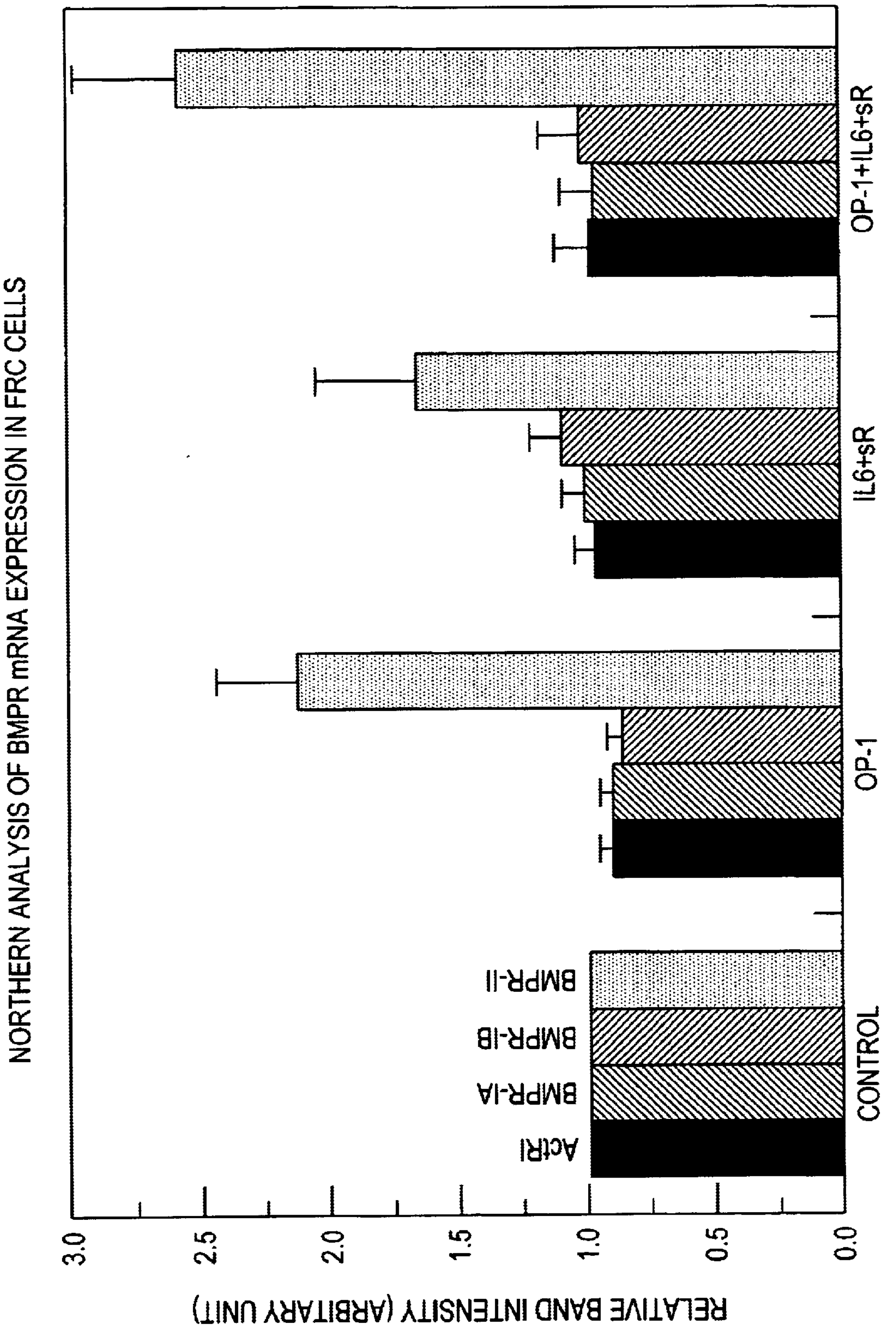
FIG. 4 is a bar graph showing the mRNA levels of BMPR-IA, BMPR-IB, ActR-I, and BMPR-II in various test groups. "sR" stands for sIL-6R. Values in the graph represent the means±SE of twelve Northern blots with RNA isolated from two different FRC cell preparations.

The mRNA levels in control FRC cells, OP-1-treated cells, IL-6/R-treated cells, and (OP-1+IL-6/R)-treated cells were compared (FIG. 4). The data showed that OP-1 did not affect the mRNA level of the type 1 receptors, but stimulated the BMPR-II mRNA level by about 2.2 fold. Likewise, IL-6/R did not alter the mRNA expression level of the type I receptors, but increased the BMPR-II mRNA level by about 1.5-fold. In the presence of OP-1 and IL-6/R, the mRNA level of the type I receptors was not significantly changed; however, the BMPR-II mRNA level was almost 3-fold higher than the control. These results suggest that IL-6/R can stimulate the osteogenic activity of OP-1 by elevating BMPR-II mRNA expression.

Example 5

The OP-1 protein used in Examples 1–4 was provided exogenously to the test cells. To investigate whether the same IL-6/R synergistic effect would be observed when the OP-1 protein was expressed intracellularly in test cells, FRC cells were transfected with pW24, a plasmid carrying an OP-1 coding sequence under the control of the CMV promoter.

Figure 5:
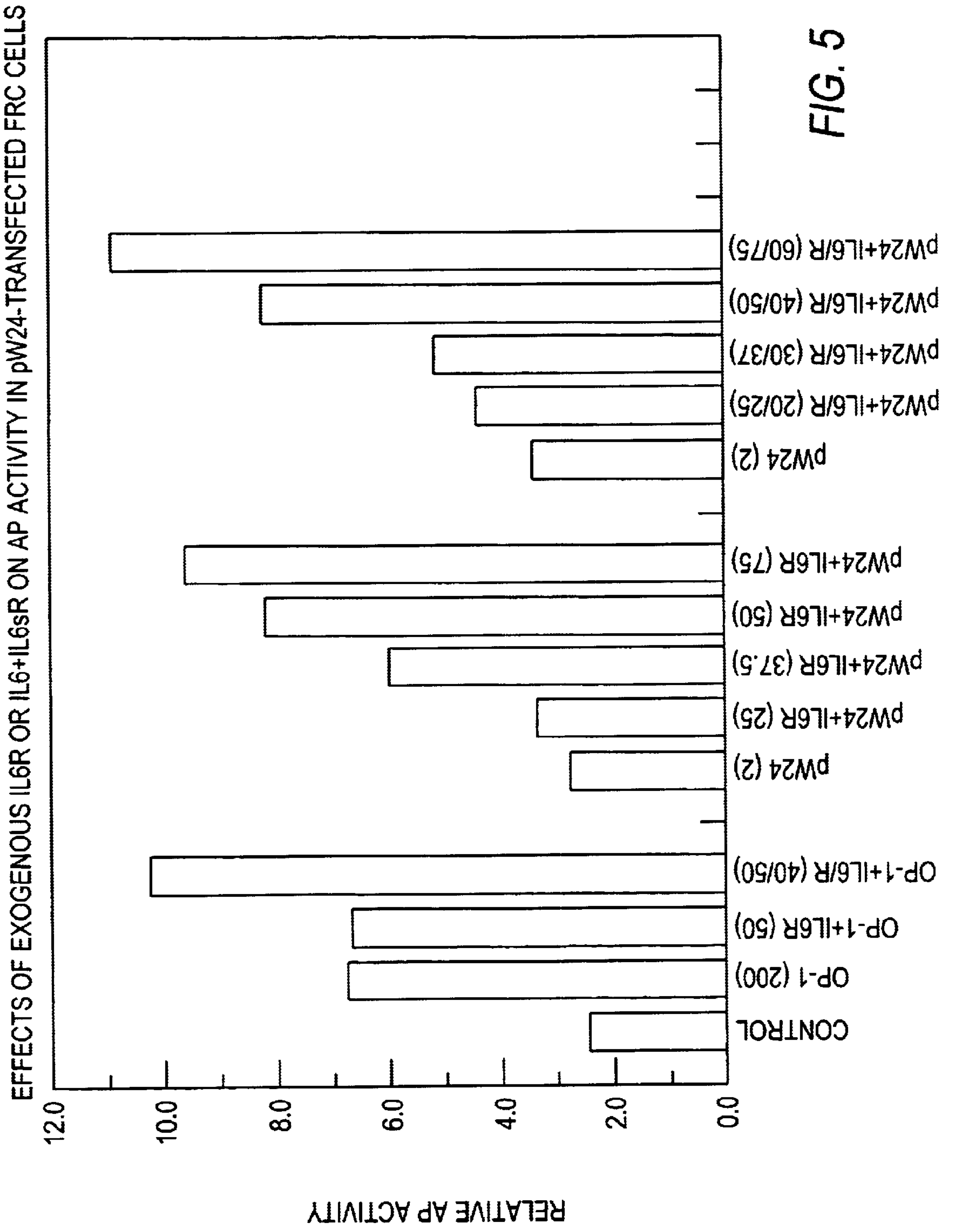
FIG. 5 is a bar graph showing that the AP activity in FRC cells transfected with the OP-1-encoding pW24 plasmid is enhanced by exogenous sIL-6R alone or a combination of IL-6 and sIL-6R ("IL-6/R"). "IL6R" stands for sIL-6R. Values in the graph represent the mean±SE of five independent determinations with three different FRC cell preparations and two different DNA preparations. "IL-6/R (X/Y)" refers to X ng/ml IL-6 and Y ng/ml sIL-6R.

Briefly, confluent FRC cells were transfected with pW24 (2 μg/ml). After recovery, the transfected cells were treated with exogenous sIL-6R alone or IL-6/R for 24 hours. Then the total AP activity levels were determined (FIG. 5).

The data showed that the levels of OP-1-induced AP activity in pW24-transfected cells were enhanced by sIL-6R in a dose-dependent manner. At a concentration of 75 ng/ml, sIL-6R stimulated the OP-1-induced AP activity by as much as 4 fold.

The data also showed that the levels of OP-1-induced AP activity in pW24-transfected cells were also enhanced by IL-6/R in a dose-dependent manner. A 2.5-fold stimulation of the OP-1-induced AP activity was observed when EL-6/R was applied to the test cells at concentrations of 60 ng/ml for IL-6 and 75 ng/ml for sIL-6R.

What is claimed is:

1. A method for improving the tissue inductive capability of an osteogenic protein at a target locus in a mammal selected from the group consisting of bone, cartilage, tendon/ligament, and neural tissue, the method comprising administering to the target locus the osteogenic protein and a first effective amount of IL-6 and a second effective amount of a soluble IL-6 receptor, wherein the osteogenic protein has tissue inductive activity when accessible to a progenitor cell in the mammal, and IL-6 and the soluble IL-6 receptor in combination synergistically enhance the tissue inductive activity of the osteogenic protein.

2. The method of claim 1, wherein the osteogenic protein comprises a pair of subunits disulfide-bonded to produce a dimeric species, wherein at least one of the subunits comprises a polypeptide belonging to the BMP protein family.

3. The method of claim 1, wherein the osteogenic protein is capable of inducing the progenitor cell to form endochondral or intramembranous bone.

4. The method of claim 1, wherein the osteogenic protein is capable of inducing the progenitor cell to form cartilage.

5. The method of claim 1, wherein the osteogenic protein is capable of inducing the progenitor cell to form tissue tendon/ligament-like or neural-like tissue.

6. The method of claim 1, wherein osteogenic protein comprises an amino acid sequence at least 70% homologous to the amino acid sequence of BMP-2, BMP-3, BMP-4, BMP-5, BMP-6, BMP-7 (OP-1), BMP-8, BMP-9, BMP-10, BMP-11, BMP-12, BMP-13, COP-5, or COP-7.

7. The method of claim 6, wherein the osteogenic protein comprises a polypeptide selected from the group consisting of OP-1, BMP-2, BMP-4 and BMP-6.

8. The method of claim 7, wherein the osteogenic protein is OP-1.

9. The method of claim 2, wherein the dimer is a homo- or heterodimer comprising a BMP-2 or BMP-7 (OP-1) subunit.

10. The method of claim 1, wherein the osteogenic protein, IL-6, and the soluble IL-6 receptor are administered simultaneously to the target locus.

11. The method of claim 1, wherein the osteogenic protein, IL-6, and the soluble IL-6 receptor are administered separately to the target locus.

12. The method of claim 1, wherein IL-6 and the soluble IL-6 receptor are administered simultaneously to the target locus.

13. The method of claim 1, wherein the target locus is a jaw bone defect.

14. The method of claim 1, wherein the target locus is a bone defect selected from the group consisting of a fracture, a non-union fracture, a critical size defect, a non-critical size defect, an osteochondral defect, a fusion and a bony void.

15. The method of claim 1, wherein the target locus has a tissue degenerative condition.

16. The method of claim 1, wherein the target locus is a cartilage or soft tissue defect.

17. The method of claim 1, wherein the target locus is a neural tissue defect.

18. The method of claim 1, wherein the osteogenic protein is administered in a matrix-comprising carrier.

19. The method of claim 18, wherein the carrier comprises allogenic bone.

20. A pharmaceutical composition for inducing tissue formation selected from the group consisting of bone formation, cartilage formation, tendon/ligament formation and neural tissue formation in a mammal, comprising an osteogenic protein, IL-6 and a soluble IL-6 receptor, wherein the osteogenic protein has tissue inductive activity when accessible to a progenitor cell in the mammal, and IL-6 and the soluble IL-6 receptor in combination synergistically enhance the tissue inductive activity of the osteogenic protein.

21. The pharmaceutical composition of claim 20, further comprising an implantable, biocompatible carrier.

22. The pharmaceutical composition of claim 21, wherein the carrier comprises demineralized, protein-extracted, particulate, allogenic bone.

23. The pharmaceutical composition of claim 21, wherein the carrier comprises mineral-free, delipidated Type I insoluble bone collagen particles, substantially depleted in noncollagenous protein.

24. The pharmaceutical composition of claim 20, wherein the osteogenic protein comprises an amino acid sequence at least 70% homologous to the amino acid sequence of BMP-2, BMP-3, BMP-4, BMP-5, BMP-6, BMP-7 (OP-1), BMP-8, BMP-9, BMP-10, BMP-11, BMP-12, BMP-13, COP-5, or COP-7.

25. The pharmaceutical composition of claim 24, wherein the osteogenic protein is human OP-1.

26. A kit for inducing tissue formation selected from the group consisting of bone formation, cartilage formation, tendon/ligament formation and neural tissue formation in a mammal, comprising a first receptacle containing a osteogenic protein, a second receptacle containing IL-6, and a third receptacle containing a soluble IL-6 receptor, wherein the osteogenic protein has tissue inductive activity when accessible to a progenitor cell in the mammal, and IL-6 and the soluble IL-6 receptor in combination synergistically enhance the tissue inductive activity of the osteogenic protein.

27. The kit of claim 26, wherein the second and the third receptacles are the same.

* * * * *

UNITED STATES PATENT AND TRADEMARK OFFICE

CERTIFICATE OF CORRECTION

PATENT NO. : 6,696,410 B1 
DATED : February 24, 2004
INVENTOR(S) : John C. Lee et al.

It is certified that error appears in the above-identified patent and that said Letters Patent is hereby corrected as shown below:

Column 9,
Line 40, change "Glu) ," to -- Glu) ; --.

Column 11,
Line 4, change "Ile," to -- Ile; --.

Columns 11 and 12,
The chart showing the amino acid sequence "OPX", change amino acid residue 77 from "VaI" to -- Val --.

Columns 13 and 14,
SEQ ID NO: 14, amino acid sequence, change residue 19, from "J" to -- I --.

Column 13,
Line 47, change "formamtide" to -- formamide --.

Column 18,
Line 52, change "Mukhedjee" to -- Mukherjee --.

Column 19,
Line 52, change "site," to -- site; --.

Column 20,
Line 25, change "osteogernc" to -- osteogenic --.
Line 38, change "DVGWDDWIVAPPGYQAFYCHGECPFPLAD" to
-- DVGWDDWIVAPPGYQAFYCHGECPFPLAD --.
Line 40, change "DVGWNDWIVAPPGYHAFYCHGECPFPLAD" to
-- DVGWNDWIVAPPGYHAFYCHGECPFPLAD --.
Line 42, change "HFNSTN" to -- HFNSTN --.
Line 44, change "HLNSTN" to -- HLNSTN --.

Column 22,
Line 44, change "fall" to -- full --.
Line 45, change "(26 ID)" to -- (26 kD) --.
Line 45, change "E:" to -- E. --.

UNITED STATES PATENT AND TRADEMARK OFFICE

CERTIFICATE OF CORRECTION

PATENT NO. : 6,696,410 B1
DATED : February 24, 2004
INVENTOR(S) : John C. Lee et al.

It is certified that error appears in the above-identified patent and that said Letters Patent is hereby corrected as shown below:

Column 23,
Line 16, change “Morphogehic” to -- Morphogenic --.

Column 28,
Line 12, change “of;” to -- of, --.

Column 32,
Line 65, change “EL-6/R” to -- IL-6/R --.

Signed and Sealed this

Twenty-fifth Day of January, 2005

JON W. DUDAS
*Director of the United States Patent and Trademark Office*